(12) United States Patent
Ja

(10) Patent No.: US 12,744,117 B2
(45) Date of Patent: Sep. 22, 2026

(54) SYSTEMS AND METHODS FOR INCREASING THREE-DIMENSIONAL IMAGE QUALITY USING MORPHOLOGY-BASED RECOMPOSITION

(71) Applicant: Araceli Biosciences Inc., Tigard, OR (US)

(72) Inventor: Shiou-jyh Ja, Portland, OR (US)

(73) Assignee: ARACELI BIOSCIENCES INC., Tigard, OR (US)

( * ) Notice: Subject to any disclaimer, the term of this patent is extended or adjusted under 35 U.S.C. 154(b) by 265 days.

(21) Appl. No.: 18/742,952

(22) Filed: Jun. 13, 2024

(65) Prior Publication Data

US 2025/0384990 A1 Dec. 18, 2025

(51) Int. Cl.

| | |
|---|---|
| ***G06T 15/00*** | (2011.01) |
| ***G06T 3/40*** | (2006.01) |
| ***G06T 5/50*** | (2006.01) |
| ***G16H 30/40*** | (2018.01) |

(52) U.S. Cl.

CPC .............. *G16H 30/40* (2018.01); *G06T 3/40* (2013.01); *G06T 5/50* (2013.01); *G06T 15/00* (2013.01); *G06T 2207/10056* (2013.01); *G06T 2207/10064* (2013.01); *G06T 2207/20036* (2013.01); *G06T 2207/20224* (2013.01)

(58) Field of Classification Search

CPC .. G16H 30/40; G06T 3/40; G06T 5/50; G06T 15/00; G06T 2207/10056; G06T 2207/10064; G06T 2207/20036; G06T 2207/20224; G06T 17/00

See application file for complete search history.

(56) References Cited

U.S. PATENT DOCUMENTS

2007/0177825 A1* 8/2007 Suzuki .................... G06T 7/155 382/308
2017/0084012 A1* 3/2017 Walle-Jensen ........... G06T 5/92
2019/0172188 A1* 6/2019 Schmidt ................ A61B 6/032
2021/0035338 A1* 2/2021 Zhou ..................... G06N 3/084
2021/0279861 A1* 9/2021 Macmahon .......... G06T 7/0012

(Continued)

FOREIGN PATENT DOCUMENTS

KR 20230136003 A 9/2023

OTHER PUBLICATIONS

Román, J. et al., “Entropy and Contrast Enhancement of Infrared Thermal Images Using the Multiscale Top-Hat Transform,” Entropy (Basel), vol. 21, No. 3, Mar. 4, 2019, 19 pages.

(Continued)

*Primary Examiner* — Syed Haider
(74) *Attorney, Agent, or Firm* — McCoy Russell LLP

(57) ABSTRACT

Methods and systems are provided herein for generating a morphology-based recomposition based on 3-dimensional input image data including an image stack of 2-dimensional (2D) images, the morphology-based recomposition being a final image generated by performing one or more white top hat (WTH) transforms on each 2D image, generating two or more image layers based on two or more WTH transformed images, and scaling adjacent image layers based on one or more scaling factors, each scaling factor being based on an estimated point spread function (PSF), two structure element sizes, and standard deviations of the estimated PSF and image data.

20 Claims, 18 Drawing Sheets

(56) References Cited

U.S. PATENT DOCUMENTS

| | | | | |
|---|---|---|---|---|
| 2022/0408024 | A1 | 12/2022 | Walden, II et al. | |
| 2023/0052595 | A1* | 2/2023 | Langoju | G06T 5/73 |
| 2023/0184683 | A1* | 6/2023 | Gutierrez | G02B 21/26 250/459.1 |
| 2023/0296873 | A1 | 9/2023 | Policelli et al. | |
| 2024/0005451 | A1* | 1/2024 | Patil | G06T 3/4046 |
| 2024/0212096 | A1* | 6/2024 | M P | G06T 3/4092 |

OTHER PUBLICATIONS

Vinegoni, C. et al., “Fluorescence microscopy tensor imaging representations for large-scale dataset analysis,” Scientific Reports, vol. 10, No. 5632, Mar. 27, 2020, 15 pages.

ISA Korean Intellectual Property Office, International Search Report and Written Opinion Issued in Application No. PCT/US2025/032326, Sep. 5, 2025, WIPO, 9 pages.

Park, H. et al., “Decomposition of Structuring Elements for Optimal Implementation of Morphological Operations,” Proceedings of the 1997 International Workshop on Nonlinear Signal and Image Processin, Sep. 10, 1997, Mackinac Island, Michigan, 5 pages.

“Richardson-Lucy deconvolution,” Wikipedia Website, Available Online at https://en.wikipedia.org/wiki/Richardson%E2%80%93Lucy_deconvolution, Page Created Sep. 12, 2005, 3 pages.

“Top-hat transform,” Wikipedia Website, Available Online at https://en.wikipedia.org/wiki/Top-hat_transform, Page Created Jul. 8, 2008, 4 pages.

Ja, S., “System and Methods for Increasing Image Quality Using a Morphological-Based Compositionm” U.S. Appl. No. 18/472,082, filed Sep. 21, 2023, 55 pages.

* cited by examiner

SYSTEMS AND METHODS FOR INCREASING THREE-DIMENSIONAL IMAGE QUALITY USING MORPHOLOGY-BASED RECOMPOSITION

FIELD

Embodiments of the subject matter disclosed herein relate generally to three-dimensional image quality and morphology-based recompositions.

BACKGROUND/SUMMARY

Various imaging technologies, such as microscopy techniques, may be used to acquire digital images of volumetric samples such as cells, biological structures, or other materials. Due to the diffractive nature of light fields and aberration of an optical imaging system, resolution of an acquired image and image quality may be reduced. More specifically, high frequency details including edges and corners in a dark-field digital image acquired with a fluorescence microscope may be rounded and small feature attenuated due to a limited spatial frequency response imposed by the imaging system. Additionally, the image may include excessive background intensity variation, which may be due to the system noise, stray light, non-uniform illumination, or emissions from defocused objects in the sample volume.

3D image datasets of volumetric samples may comprise a stack of two dimensional (2D) images taken at different focal planes with a step size therebetween along a stacking axis. A 2D deconvolution method may be applied to each of the 2D images in the stack to increase image resolution. For example, one approach for restoring resolution of the acquired image stack is by implementing a 2D deconvolution to each of the 2D images in the stack based on a known point spread function (PSF). In particular, the Richardson-Lucy deconvolution algorithm may be implemented to restore resolution of the acquired image. While the Richardson-Lucy deconvolution algorithm and similar methods have been used to restore image resolution, the degree wherein image resolution may be restored using deconvolution approaches may be limited. For example, restoration of image resolution using 2D deconvolution may be reduced due to a presence of noise and background intensity variation in the acquired image. 2D deconvolution is unable to remove a highly defocused image in the background and may cause undesired noise amplification and out-of-focus content in a final image.

Further, the Richardson-Lucy deconvolution algorithm relies on a user-provided PSF. The use of an incorrect PSF may result in the presence of undesired distortion in the final image. As such, the deconvolution algorithm relies on a correct PSF. However, the process for determining the PSF accurately may be time intensive. Additionally, the iterative nature of the Richardson-Lucy deconvolution algorithm introduces uncertainty regarding the computation time since termination criteria may be difficult to determine. An early termination may not achieve a desired increase in resolution of the acquired image whereas a later termination may cause undesired out-of-focus content, such as noise amplification, a dark halo, or an intensity ringing effect wherein periodic intensity undulation-like ripples appear around edges of a bright object. The disadvantages may be alleviated by user intervention. User intervention may include addressing undesired out-of-focus content in a trial-and-error manner, which may increase the time duration of image processing and renders automation of image processing unlikely.

Further still, due to the three-dimensional (3D) nature of a volumetric sample, the PSF may be elongated along an optical axis (e.g., axis along which light travels to and from the sample) and excessive scattered light from outside of an intended focal plane may reach the sensor, thereby reducing image contrast. Such a non-isotropic PSF may be produced by a spherical aberration induced by refractive index (RI) discontinuity between an objective lens of the imaging system and the sample. Thus, image quality of a 3D sample may be reduced due to a lower resolution along the optical axis, which 2D deconvolution methods such as Richardson-Lucy deconvolution may not address.

The inventors herein have recognized the above-mentioned issues and have engineered a way to at least partially address them. In one example, a method may include generating a morphology-based recomposition based on an input image, the morphology-based recomposition being a final image generated by performing two or more white top hat (WTH) transforms on the input image, generating two or more image layers based on two or more WTH transformed images, and scaling the intensity of the adjacent image layers based on one or more scaling factors, each scaling factor being based on an estimated point spread function (PSF), two structure element sizes, and the image data. In this way, relevant structures in the image may be extracted based on size, shape, and intensity level with an estimated PSF, which may enable layers of the input to be extracted. By applying specific weights or scaling factors to the layers, image restoration comparable to or surpassing deconvolution-based algorithms may be achieved. The disclosed methods may be less sensitive to the accuracy of the estimated PSF.

Advantages that may be realized in practicing the above-described method include decreased background interference and/or other undesired image out-of-focus content due to additional image processing and increased resolution of an acquired image without significant burden on the user. In particular, by knowing a rough size of the PSF and structures within the image that may be refined, the out-of-focus image and other background intensity issues due to vignetting or non-uniform illumination may be minimized and/or removed. Since the method may be performed with minimal knowledge of the user, burden on the user may be minimized when compared to deconvolution-based algorithms. In addition, the method is compatible with GPU processing and may be performed in parallel, which may result in acceptable image processing times (e.g., a fraction of a second). Moreover, by applying morphology-based recomposition in all three dimensions of a 3D image dataset, resolution along the stacking axis of an image stack may be increased. Further, when applying 2D morphology-based recomposition to each image in an image stack, the step size between 2D images of the image stack may be regular (e.g., approximately the same between any two adjacent 2D images) or irregular (e.g., different step sizes between different adjacent pairs of 2D images). Further still, by reducing out-of-focus image and other background intensity issues with morphology-based recomposition, a "2.5 dimensional" (2.5D) image dataset (e.g., a small image stack with a small dimension along the stacking axis) may be prepared for an integration or projection, such as maximum intensity projection (MIP), in such a way where resolution and contrast of the image following the integration or projection may be increased.

The above advantages and other advantages, and features of the present description will be readily apparent from the following detailed description when taken alone or in connection with the accompanying drawings.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

DETAILED DESCRIPTION

Figure 2:
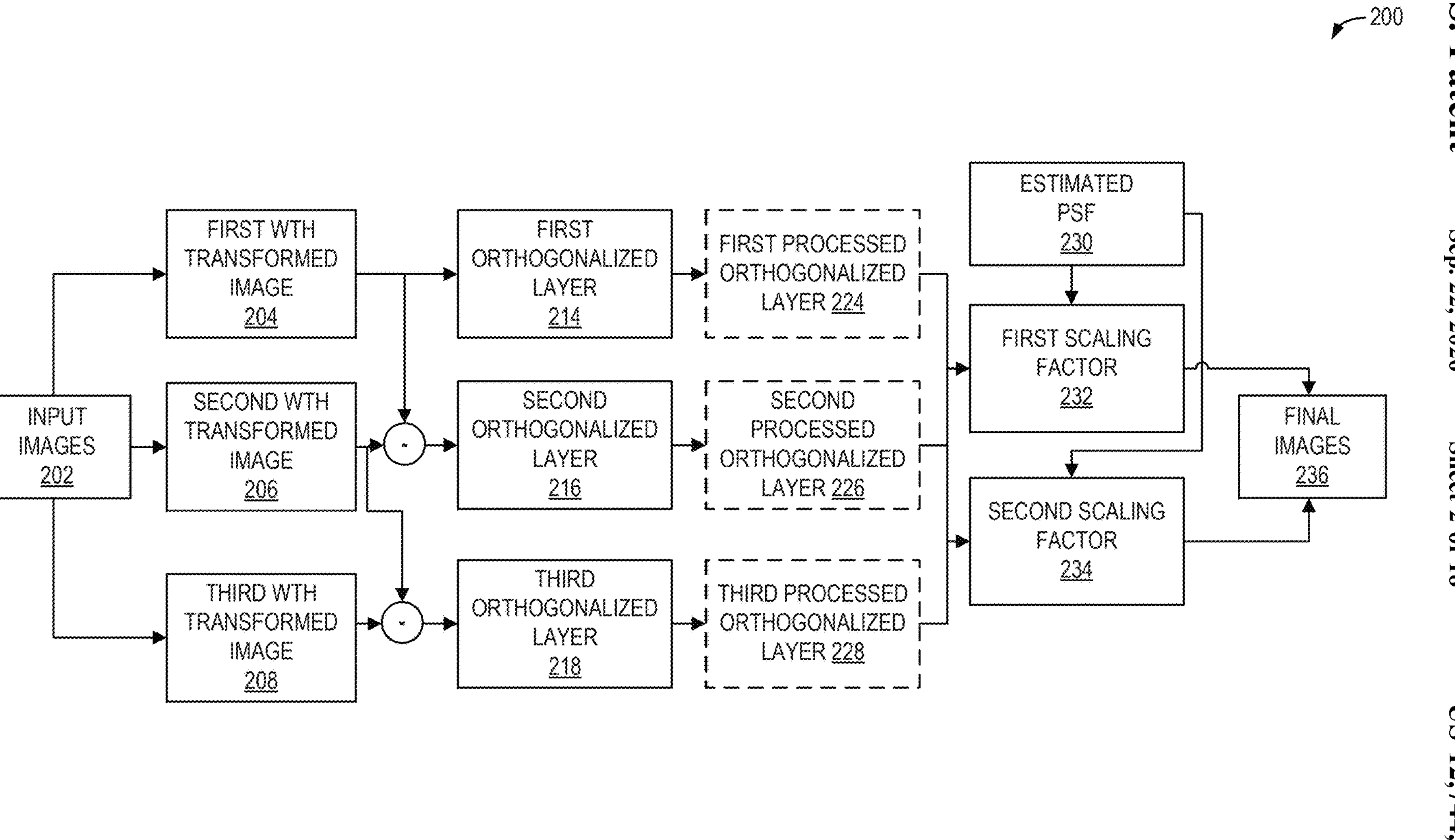
FIG. 2 shows a block diagram of a process for increasing image resolution using a morphology-based recomposition.
Figure 3:
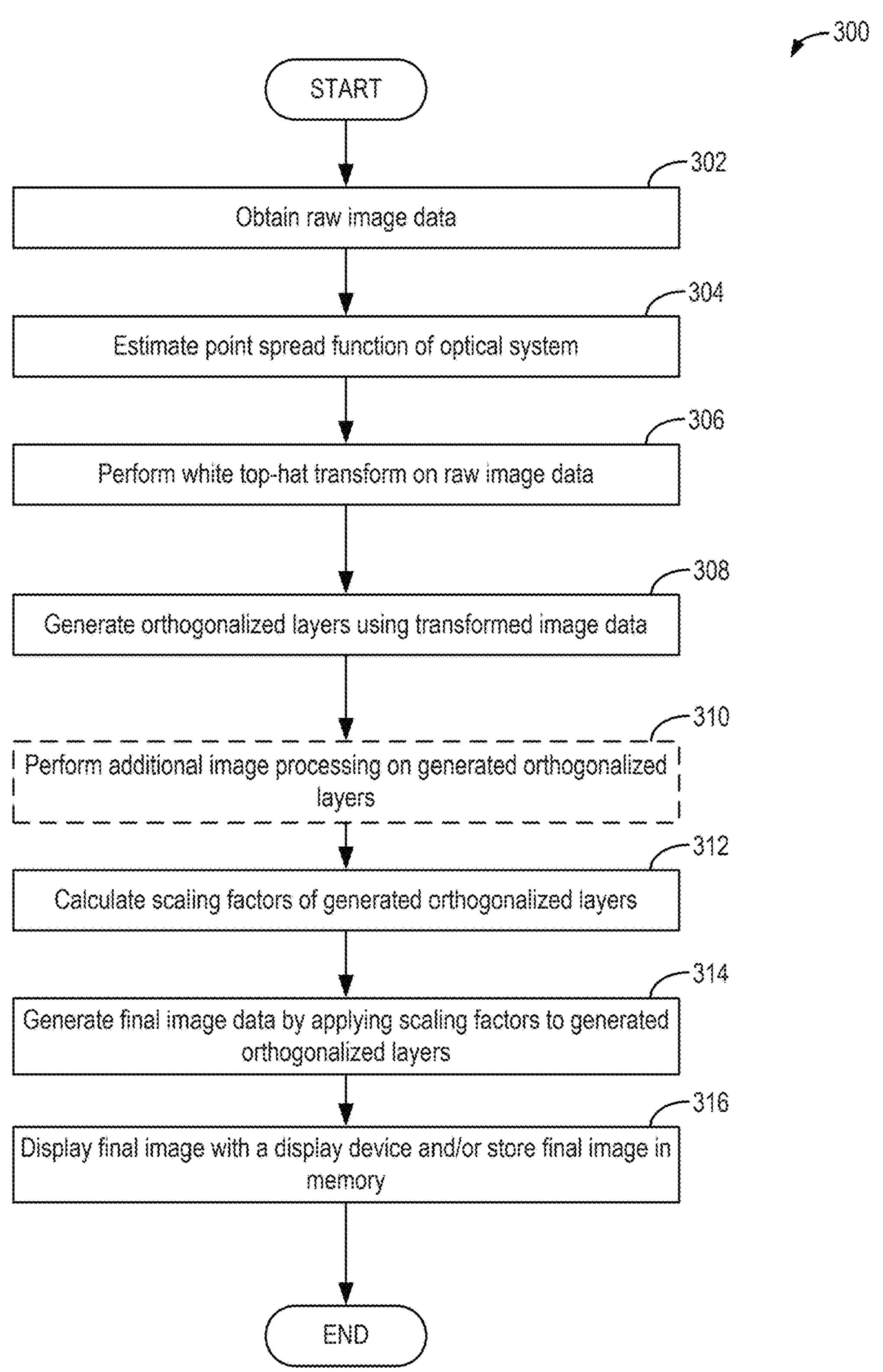
FIG. 3 shows a flow chart of an example method for generating a morphology-based recomposition to increase image resolution.
Figures 8A, 8B:
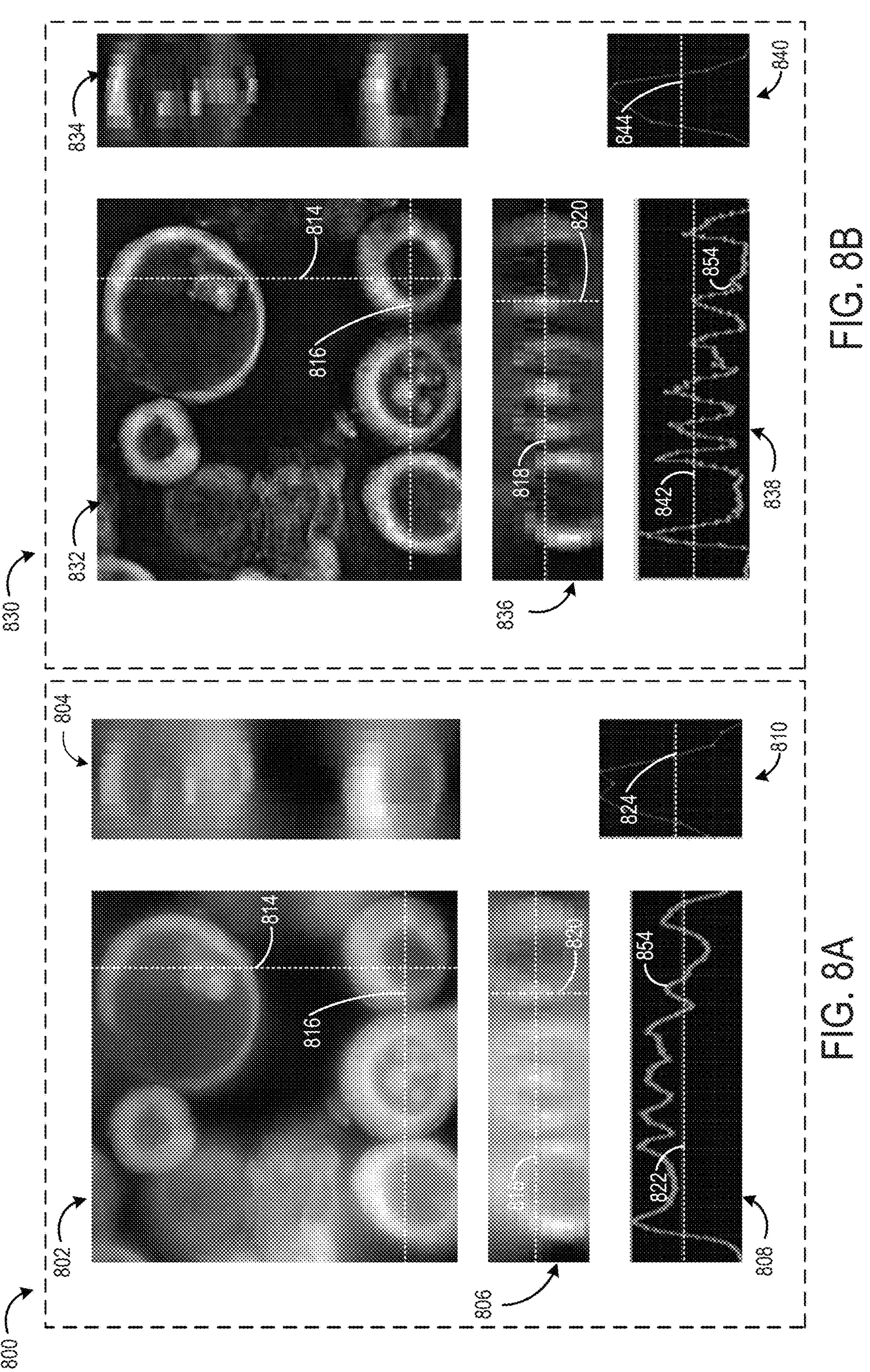
FIGS. 8A-8C show a second example of implementing morphology-based recomposition using a 3D image dataset.
Figure 8C:
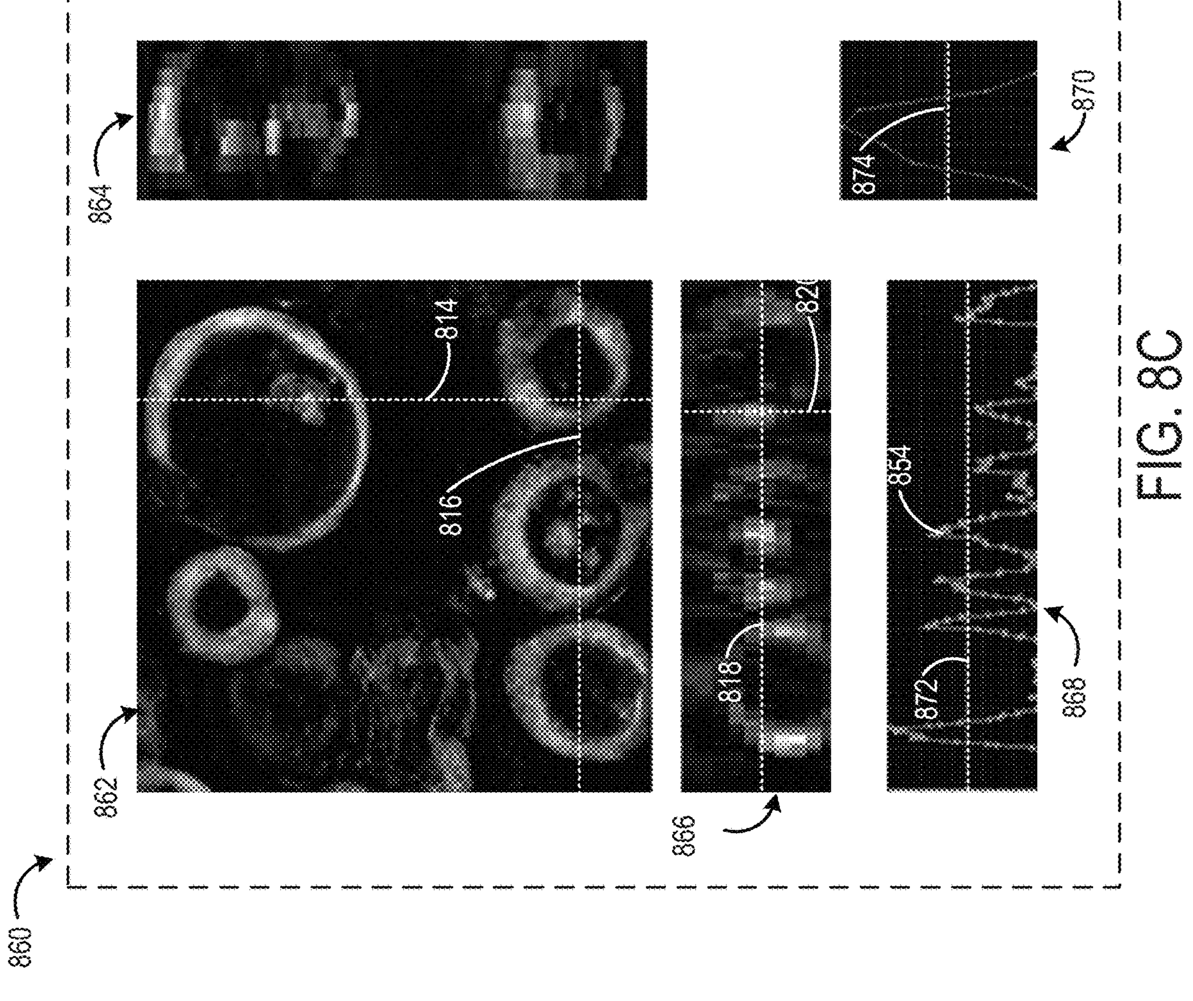
Figure 9:
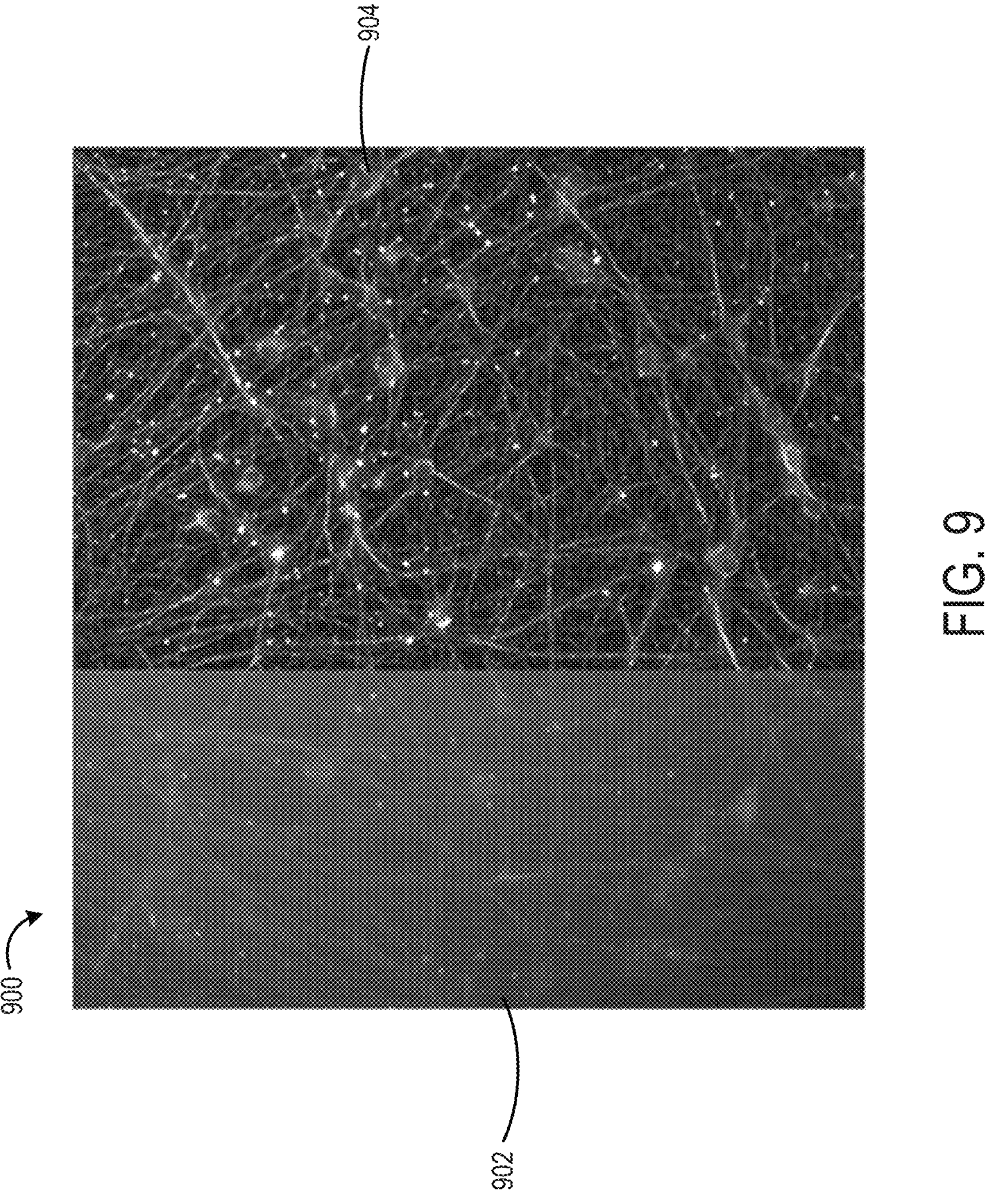
FIG. 9 shows an example of implementing morphology-based recomposition on a small image stack referred to as a "2.5-dimensional" (2.5D) image dataset.
Figures 10A, 10B:
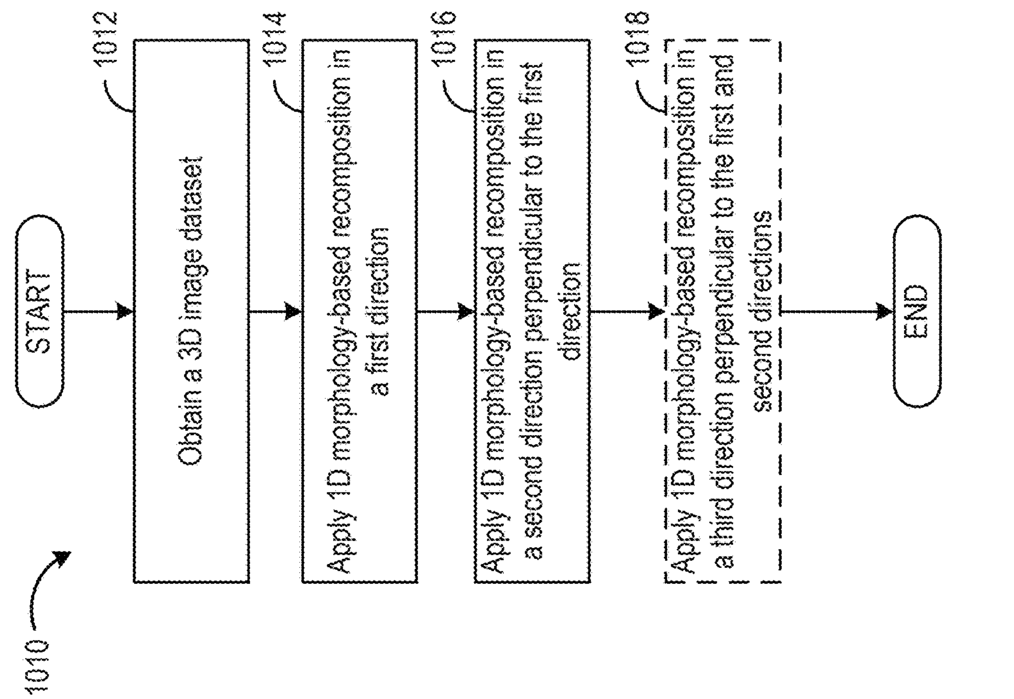
FIGS. 10A and 10B show block diagrams for increasing image resolution of 3D image datasets using morphology-based recomposition.
Figure 11:
FIG. 11 shows a block diagram for increasing resolution of a 2.5D image dataset.
Figure 11:
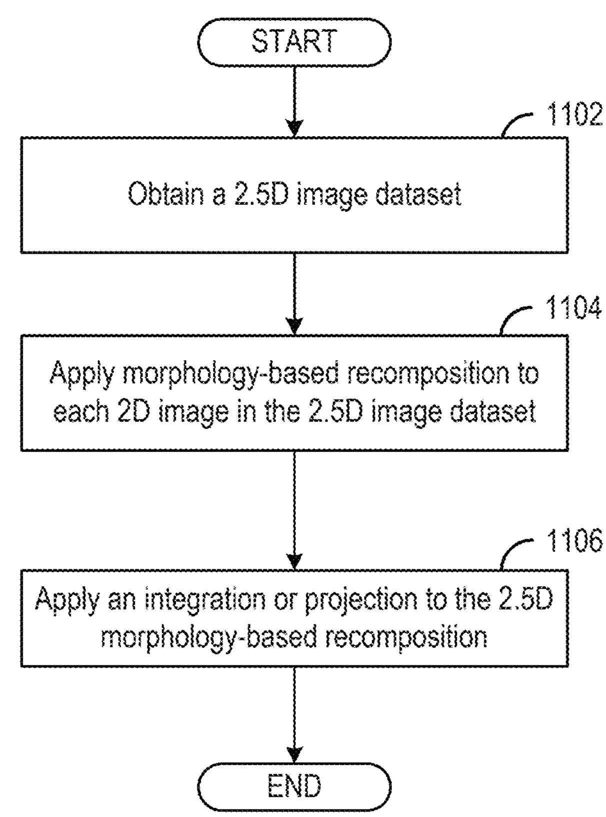

The present description is related to systems and methods for increasing 3-dimensional (3D) image dataset quality by generating morphology-based recompositions based on an input image stack comprising a plurality of two-dimensional (2D) images with a step size along a third axis (e.g., a stacking axis along which the 2D images are stacked perpendicularly thereto). Methods for increasing image quality with morphology-based recompositions may be performed using a computing system, such as the computing system shown in FIG. 1. A process for generating a morphology-based recomposition to increase image resolution is shown in FIG. 2. FIG. 3 illustrates a method for generating the morphology-based recomposition based on an input image (e.g., a 3D fluorescent microscopy input image dataset). FIGS. 4A-4F show examples of a 2D phantom image, example of final images generated with 2D deconvolution and according to the embodiments described herein, and a plurality of 2D white top hot transforms performed on the 2D phantom image according to the method described herein. FIGS. 5A-5D show a first example of generating a morphology-based recomposition based on a 2D phantom image. FIGS. 6A-6D show a second example of generating a morphology-based recomposition based on a 2D phantom image. FIGS. 10A and 10B show block diagrams of methods for applying morphology-based recomposition to 3D image datasets. FIGS. 7A-7E show a first example of generating a morphology-based recomposition based on a 3D image dataset. FIGS. 8A-8C show a second example of generating a morphology-based recomposition based on a 3D image dataset. FIG. 11 shows a block diagram of a method for applying morphology-based recomposition to a "2.5-dimensional (2.5D) image dataset", wherein a 2.5D image dataset comprises a thickness greater than a focal plane of a 2D image but not large enough to produce a 3D image. FIG. 9 shows an example of generating a morphology based recomposition based on a 2.5D image dataset.

Figure 1:
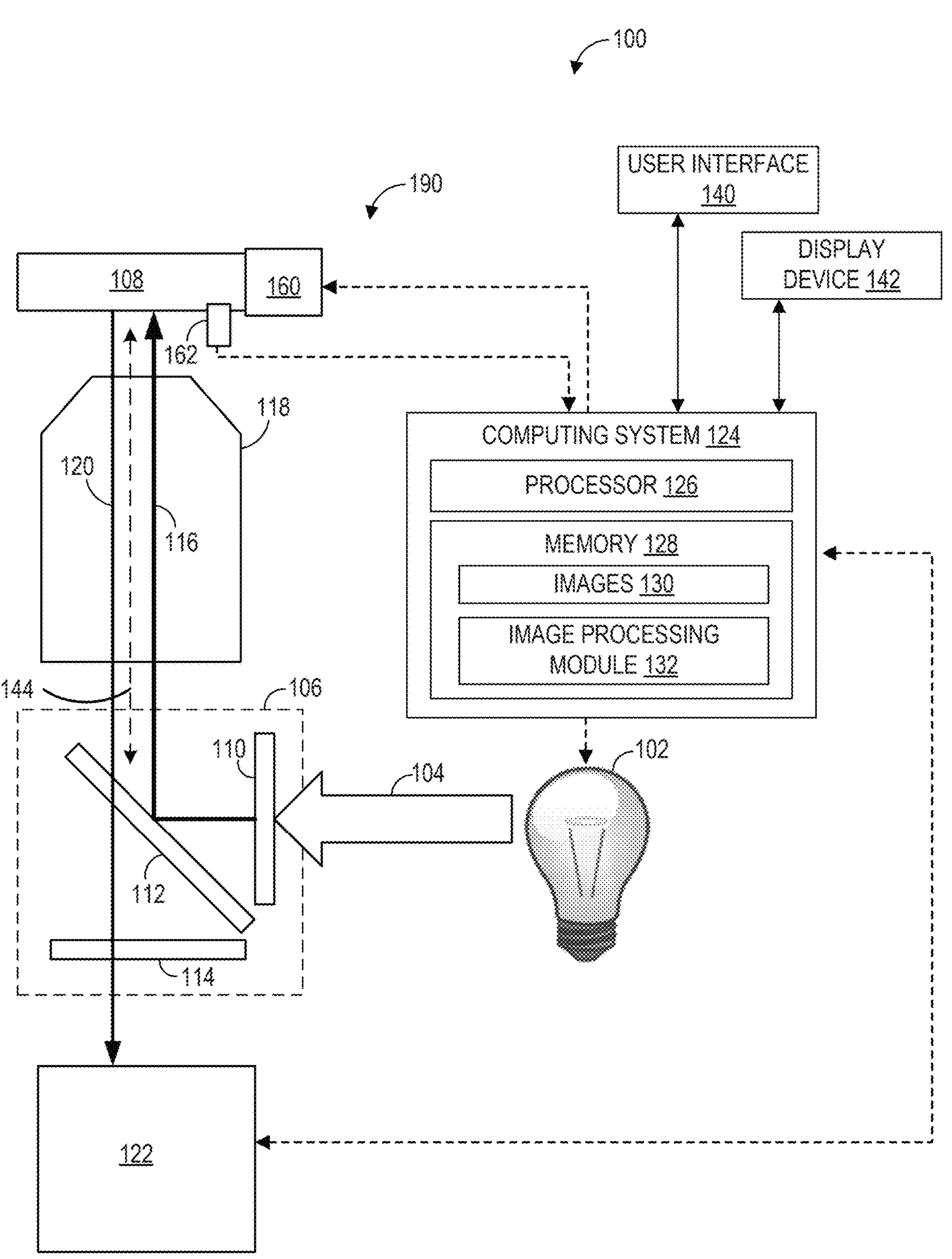
FIG. 1 shows a diagram of a computing device.

Turning now to FIG. 1, a schematic diagram for a system 100 is shown. In one example, the system 100 may be configured as a wide-field microscopy system, such as a fluorescence microscopy system as herein described, though other configurations of the system 100 are possible. An imager 190 of the system 100 may include a light source 102 providing incident light to components arranged in a path of the incident light, as indicated by arrow 104. The light source 102 may be a mercury-vapor lamp, a xenon arc lamp, a laser, or one or more light-emitting diodes (LEDs). In some examples, the system 100 may be included in a multi-detector microscope system.

The incident light may be directed to a filter cube 106 (e.g., also called a filter block). The filter cube 106 may house components that filter the incident light such that target wavelengths are transmitted to a target to be analyzed, e.g., one or more samples supported on a sample holder 108. In one example, the sample holder 108 may be a microplate. In the example of FIG. 1, three filtering components are arranged in the filter cube 106, including an excitation filter 110, a dichroic filter 112, and an emission filter 114. The incident light may first pass through the excitation filter 110 which filters the light to allow select, e.g., target, wavelengths to continue past the excitation filter 110 and block other wavelengths of light. The target wavelengths may be wavelengths that excite electrons in specific fluorophores or fluorochromes, resulting in release of photons when the excited electrons relax to a ground state.

The excitation light, e.g., light that has been filtered by the excitation filter 110, then strikes the dichroic filter 112 (or dichroic beam splitter), as indicated by arrow 116. Light traveling to and from the sample holder 108 may be oriented parallel with an optical axis 144 extending between the detector 122 and the sample holder 108. The dichroic filter 112 may be a mirror, for example, arranged at a 45 degree angle relative to an optical path of the system 100, e.g., angled at 45 degrees relative to the path of incident light indicated by arrow 104. A surface of the dichroic filter 112 may include a coating that reflects the excitation light, e.g., light filtered by the excitation filter 110, but allows fluorescence emitted from the sample at the sample holder 108 to pass therethrough. The reflected excitation light, as indicated by arrow 116, passes through an objective lens 118 to illuminate the sample holder 108. If the sample positioned in the sample holder 108 fluoresces, light is emitted, e.g., generating emission light as indicated by arrow 120, and collected by the objective lens 118. The emission light passes through the dichroic filter 112 and continues to the emission filter 114, which blocks undesired excitation wavelengths from passing therethrough. The filtered emission light is received at a detector 122. The detector 122 may be a camera, such as a charge-coupled device (CCD) camera, in one example. In other examples, the detector 122 may be another type of camera, for example, a complementary metal-oxide-semiconductor (CMOS) camera, or a photomultiplier tube.

At the detector 122, the emission light may be converted into electronic data. For example, when the detector 122 is the CMOS camera, the detector 122 may include a light sensor configured as a transistor on an integrated circuit. Photons of the emission light may be incident on the light sensor and generate an electrical charge that is converted into electronic data representative of a photon pattern of the emission light captured within a field of view (FOV) of the imaging system. The electronic data may be stored at a memory of the camera, such as random access memory, and may be retrieved by a computing system 124.

The computing system 124 may be a computing device or other computer. The computing system 124 may include a processor 126 and a memory 128. The processor 126 may comprise one or more computational components usable for executing machine-readable instructions. For example, the processor 126 may comprise a central processing unit (CPU) or may include, for example a graphics processing unit (GPU). The processor 126 may be positioned within the computing system 124 or may be communicatively coupled to the computing system 124 via a suitable remote connection.

The memory 128 may comprise one or more types of computer-readable media, including volatile and/or non-volatile memory. The volatile memory may comprise, for example, random-access memory (RAM). The non-volatile memory may comprise, for example, read-only memory (ROM). The memory 128 may include one or more hard disk drive(s) (HDDs), solid state drives (SSDs), flash memory, and the like. The memory 128 is usable to store machine-readable instructions, which may be executed by the processor 126. The memory 128 is further configured to store images 130, which may comprise digital images captured or created using a variety of techniques, including digital imaging, digital illustration, and more. The images 130 may further include one or more reference images and/or one or more acquired images.

At least a portion of the images 130 may be acquired via the system 100. The memory 128 further includes an image processing module 132, which comprises machine-readable instructions that may be executed by the processor 126 to increase resolution of the images 130 by performing morphology-based methods to generate a morphology-based recomposition. The image processing module 132 thus contains machine-readable instructions for manipulation of digital images (e.g., the images 130), such as instructions to perform white top hat transforms on the images and generate two or more image layers that may be scaled to increase image quality and image resolution. For example, the machine-readable instructions stored in the image processing module 132 may correspond to one or more methods, examples of which are provided with respect to FIG. 3.

The system 100 further include a user interface 140, which may comprise one or more peripherals and/or input devices, including, but not limited to, a keyboard, a mouse, a touchpad, or virtually any other input device technology that is communicatively coupled to the computing system 124. The user interface 140 may enable a user interact with the computing system 124, such as to select one or more images to evaluate, to select one or more parameters of the imager 190, and so forth.

The system 100 further includes a display device 142, which may be configured to display results of resolution correction, display the images themselves, and display possible parameter options and selections related to the acquisition of images, including one or more dye wavelengths, channels, and emission spectra, for example. The user may select or otherwise input parameters via the user interface 140 based on options displayed via the display device 142.

The computing system 124 may be communicatively coupled to components of the system 100. For example, the computing system 124 may be configured to command activation/deactivation of the light source 102 when prompted based on user input. As another example, the computing system 124 may instruct adjustment of a position of the sample holder 108 to focus the excitation light on a different region of the sample holder. The computing system 124 may command actuation of a motor 160 coupled to the sample holder 108 to vary the position of the sample holder 108 with respect to the objective lens 118 and the excitation light and provide instructions on how the sample holder position is to be modified. In some examples, a position sensor 162 may monitor the actual position of the sample holder 108 and may be communicatively coupled to the computing system 124 to relay the sample holder position to the computing system 124.

The computing system 124 may also be communicatively coupled to the detector 122. As such, electronic data collected by the detector 122 may be retrieved by the computing system 124 for further processing and display at an interface, such as a computer monitor. It is to be appreciated that the computing system 124 may be further coupled to other sensors and actuators of the system 100. In one example, communication between the computing system 124 and the sensors and actuators of the system 100 may be enabled by various electronic cables, e.g., hardwiring. In other examples, the computing system 124 may communicate with the sensors and actuators via a wireless protocol, such as Wi-Fi, Bluetooth, Long Term Evolution (LTE), etc.

It will be appreciated that the system 100 depicted in FIG. 1 is a non-limiting example of a system with an imager and a computing device. Other examples may include variations in quantities of individual components, such as a number of dichroic, excitation, and emission filters, a configuration of the light source, relative positioning of the components, etc. In one example, the system 100 may be used for high through-put screening of biological samples. It should also be understood that the methods and systems herein described are not limited to microscopy systems and may be implemented for other types of imaging systems such as computerized tomography (CT), positron emission tomography (PET), magnetic resonance angiography (MRA), and more.

As illustrated in FIG. 2, a process 200 for implementing a morphology-based recomposition to increase image resolution and image quality. The process 200 includes generating a morphology-based recomposition using input images 202 that are transformed, orthogonalized, processed, and scaled, accordingly. The input images 202 may include a plurality of images acquired with florescence microscopy, for example. Thus, the input images 202 may be fluorescent microscopy images. However, input images 202 may be acquired with other imaging systems.

The input images 202 may be 1-dimensional (1D) or 2D. A 1D image may be a single row of pixels. A 2D image may comprise a plurality of rows of pixels (e.g., pixels extending along two directions). Applying 2D morphology-based recomposition may comprise performing the process 200 on one or more 2D images. Applying 1D morphology-based recomposition may comprise performing the process 200 on one or more 1D images. Further details are provided in regards to FIGS. 10A-11 as to applying 3D morphology-based recomposition to a 3D input image dataset, which may include applying 2D morphology-based recomposition and/or applying 1D morphology-based recomposition (e.g., by process 200) to subsets (e.g., a single row or a portion of the rows of pixels) of the 3D input image dataset.

Two or more white top hat (WTH) transforms may be performed on an input image in the input images 202. For example, a first white top hat (WTH) transform, a second white top hat (WTH) transform, and a third white top hat (WTH) transform may be used to generate two or more WTH transformed images, such as a first WTH transformed image 204, a second WTH transformed image 206, and a third WTH transformed image 208, respectively. The two or more WTH transformed images are generated by performing the two or more WTH transforms based on two or more structure elements wherein each structure element is a different size. For structure elements of two or more dimensions, the structure element shapes may also vary. The structure element may be either be either a binary element (e.g. a Boolean value of true or false or integer of 1 or 0) or a float point element. Among all the variations of the structure element, the size of the structure element may have the most significant effect on the result.

More specifically, the first WTH transform may be performed using a first structure element to generate the first WTH transformed image 204, the second WTH transform may be performed using a second structure element to generate the second WTH transformed image 206, and the third WTH transform may be performed using a third structure element to generate the third WTH transformed image 208. Each structure element is a different size and has a pre-determined geometry and pre-determined value.

Figure 5B:
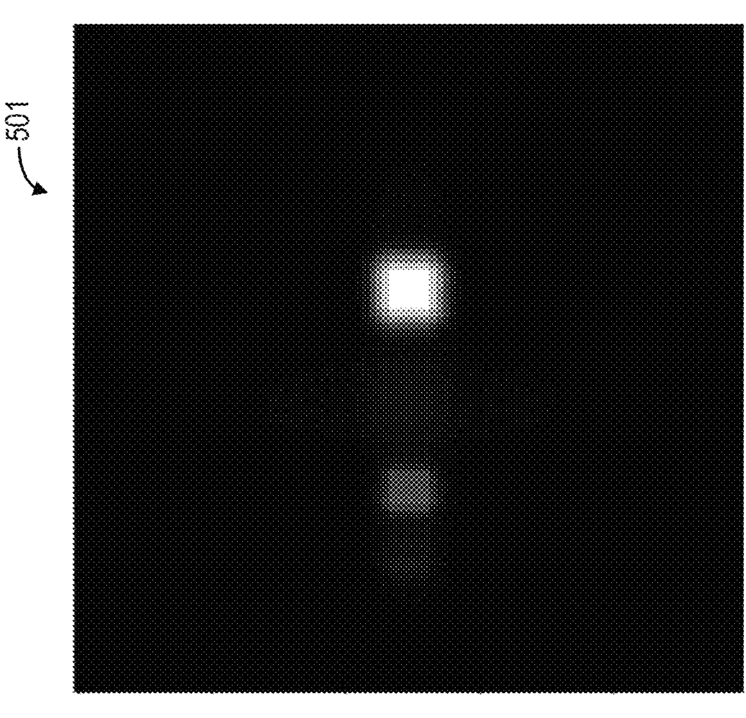
FIGS. 5A-5D show a first example of implementing a morphology-based recomposition using a 2D phantom image.
Figure 5A:
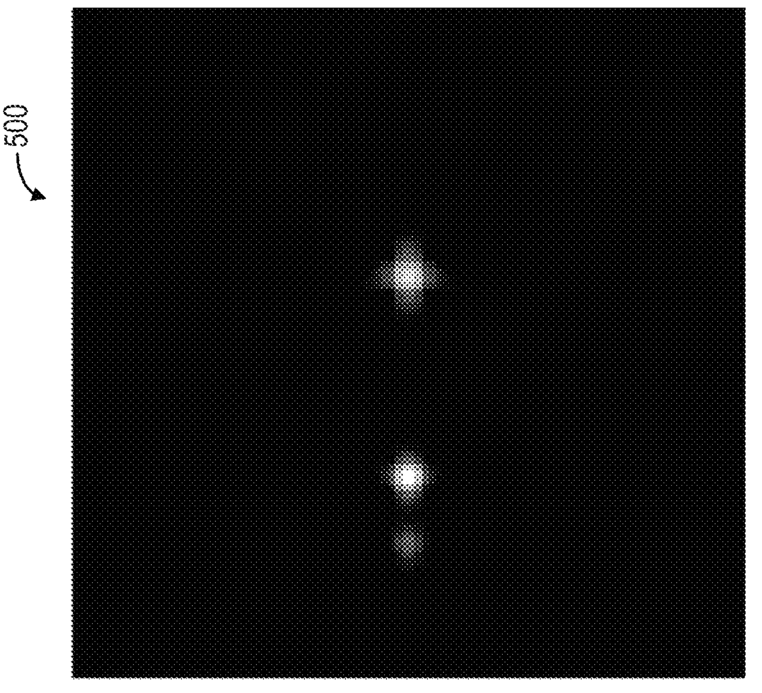

A first structure element size, a second structure element size, and a third structure element size are all different values. In this way, image features of various sizes and intensities may be extracted into different layers. In other words, the first structure element size may extract image features of a certain size in the input image, the second structure element size may extract image features of a certain size in the same input image that are different than the size of image features extracted using the first structure element size, and the third structure element size may extract image features of a certain size in the same input image that are different than the size of the image features extracted using the first structure element size and second structure element size. FIGS. 5A-5C illustrate transformed 2D images wherein various image components are extracted from a 2D phantom image.

Two or image layers may be generated based on the two or more WTH transformations. The two or more image layers may be mutually excluded to form the orthogonalized layers where each orthogonalized layer is linearly independent from the remaining orthogonalized layers. Each orthogonalized layer comprises one of a WTH transformed image generated with a smallest structure element or an image generated by subtracting one WTH transformed image with a smaller structure element from another WTH transformed image with a larger structure element. The two WTH transformed images that are subtracted from one another are generated with two different sized structure elements.

The two or more orthogonalized layers comprises one of a top layer and a base layer or the top layer, one or more intermediate layers, and the base layer. The top layer is computed with a smallest structure element and the base layer is computed with a largest structure element. As one example, the two or more orthogonalized layers may include at least the top layer and base layer when two WTH transforms are performed on the input image. As another example wherein three WTH transforms are performed on the input image, the first WTH transformed image 204, the second WTH transformed image 206, and the third WTH transformed image 208 may be orthogonalized to generate two or more orthogonalized layers that are linearly independent, such as a first orthogonalized layer 214, a second orthogonalized layer 216, and a third orthogonalized layer 218. The first orthogonalized layer 214 may be the first WTH transformed image 204. The first orthogonalized layer 214 may be the top or topmost layer. The second orthogonalized layer 216 may be generated by subtracting the first WTH transformed image 204 from the second WTH transformed image 206. The second orthogonalized layer 216 may be the intermediate layer. The third orthogonalized layer may be generated by subtracting the second WTH transformed image 206 from the third WTH transformed image 208. The third orthogonalized layer 218 may be the bottom or bottommost layer.

The process 200 may optionally include additional image processing of the first orthogonalized layer 214, the second orthogonalized layer 216, and the third orthogonalized layer 218 to generate a first processed orthogonalized layer 224, a second processed orthogonalized layer 226, and a third processed orthogonalized layer 228. The additional image processing may include denoising, intensity-based filtering, and/or other types of filtering.

The two or more processed orthogonalized image layers may be scaled to compose a final image in final images 236. The two or more processed orthogonalized layers may be scaled by calculating one or more scaling factors between pairs of adjacent orthogonalized layers, which includes an upper orthogonalized layer and a lower orthogonalized layer, and applying each of the scaling factors to the upper orthogonalized layers of the pairs to generate the final image. A scaling factor is a ratio between a respective orthogonalized layer wherein the scaling factor is applied (e.g., the upper orthogonalized layer of the pair) and a lower layer. Since each layer has been orthogonalized, there is no compound effect among the applied scaling factors. The pairs of adjacent orthogonalized layers may include one of the top layer and the base layer, the top layer and one of the one or more intermediate layers, two intermediate layers of the one or more intermediate layers, and one of the one or more intermediate layers and the base layer. A final image (e.g., a 2D image of an image stack) in final images 236 may be generated by applying each scaling factor to a respective orthogonalized layer of the pair of adjacent orthogonalized layers and composing the final image based on one or more scaled orthogonalized layers.

In an example, three orthogonalized layers, such as the first orthogonalized layer 214, the second orthogonalized layer 216, and the third orthogonalized layer 218, which may be denoted as $L_1$, $L_2$, and $L_3$, may be extracted according to the embodiments described herein. Two scaling factors, which may be donated as $S_1$ and $S_2$, respectively, are calculated for pairs of adjacent orthogonalized layers. In one embodiment, the first orthogonalized layer 214 and the second orthogonalized layer 216 may be a first pair of adjacent orthogonalized layers denoted as $L_1/L_2$ and the second orthogonalized layer 216 may be a second pair of adjacent orthogonalized layers denoted as $L_2/L_3$. The scaling factor $S_1$ may be applied to $L_1$, since $L_1$ is the upper orthogonalized layer of the first pair of adjacent orthogonalized layers and the scaling factor $S_2$ may be applied to $L_2$ since $L_2$ is the upper orthogonalized layer of the second pair of adjacent orthogonalized layers. After application of the scaling factors $S_1$ and $S_2$, the three orthogonalized layers are summed to generate a final image of final images 236.

As one example, a first scaling factor 232 between the first orthogonalized layer 214 (or first processed orthogonalized layer 224) and the second orthogonalized layer 216 (or second processed orthogonalized layer 226) may be calculated based on an estimated Point Spread Function (PSF) 230 of the imaging system to be reached. A second scaling factor 234 between the second orthogonalized layer 216 (or second processed orthogonalized layer 226) and the third orthogonalized layer 218 (or third processed orthogonalized layer 228) may be calculated based on the estimated PSF 230 to be reached. By applying the first scaling factor 232 and the second scaling factor 234, the final image in final images 236 may be generated wherein the final image is a higher quality image than the input image. The final image may be considered a morphology-based recomposition. Calculation and application of the scaling factors is described below with respect to FIG. 3.

As described above, the process 200 may be performed on 1D image data or 2D image data. For examples wherein the input images 202 are 2D, the structure element is 2D (e.g., a shape with a number of pixels in two dimensions), and 2D WTH transforms (or an appropriate equivalent of 1D WTH transforms) are performed. Thus, in such examples, the WTH transformed images 204, 206 and 208, the orthogonalized layers 214, 216, and 218, the final images 236 (and when applicable the processed orthogonalized layers 224, 226, 228) are 2D. In examples wherein the input images 202 are 1D (e.g., a single row of pixels), the structure element is 1D (e.g., a number of pixels in one dimension), and 1D WTH transforms are performed on the input images 202. Thus, in such examples, the WTH transformed images 204, 206 and 208, the orthogonalized layers 214, 216, and 218, the final images 236 (and when applicable the processed orthogonalized layers 224, 226, 228) are 1D (e.g., single row of pixels). In yet other examples, 3D image datasets may be processed with the process 200 by applying a series of 2D and/or additional 1D WTH transforms along the stacking axis (e.g. z axis) to the 3D image data. Processing 3D image datasets with the process 200 is described further below in regards to FIGS. 10A and 10B.

The process 200 described above is exemplary and does not limit the scope of the present disclosure. In other embodiments, the process 200 may include performing additional or less WTH transforms on the input image without departing from the scope of the present disclosure. Further, the process 200 may include applying additional or less scaling factors based on the number of WTH transforms of the input image.

FIG. 3 shows a method 300 for increasing resolution of an image acquired with an imaging system, such as the system 100 of FIG. 1. The method 300 may be executed by a processor of a computing system, such as the processor 126 of the computing system 124 of FIG. 1, according to instructions stored in a non-transitory memory of the computing system (e.g., within the image processing module 132 of the memory 128 of FIG. 1).

At 302, the method 300 includes obtaining input image data. Input images (e.g., a 3D image comprising a stack of 2D images) may be acquired via the imaging system during data acquisition, such as the system described above with respect to FIG. 1. The input image(s) may be obtained during the time wherein the system is actively performing high-speed image data acquisition (DAQ). In some embodiments, the input image may comprise a biological sample. The input images 202 may be 2D or 3D. Applying 2D morphology-based recomposition may comprise performing the method 300 on one or more 2D images. Applying 1D morphology-based recomposition may comprise performing the method 300 on one or more 1D images, which may be subsets of 2D or 3D image data. Further details are provided as to applying 3D morphology-based recomposition to a 3D image dataset in regards to FIGS. 10A-11, which may include applying 2D morphology-based recomposition and/or applying 1D morphology-based recomposition to subsets of the 3D image dataset.

At 304, the method 300 includes estimating a point spread function (PSF) of an optical system. The PSF may be estimated by an analytical equation based on a numerical aperture of an objective and a wavelength of the imaging system. The analytical equation may be based on known criterions, such as the Rayleigh criterion and the like, and an assumed PSF distribution function, such as the Gaussian function. In this way, the PSF may be estimated instead of measured.

At 306, the method 300 includes performing a white top-hat transform on the input image data. The white top-hat (WTH) transform may be performed according to the following equation 1:

$$WTH_i(I) = I - (I \circ SE_i) \tag{1}$$

where I is an input image, $SE_i$ is a structure element with a size of i, $\circ$ is an opening operation, and $WTH_i$, is an extracted image component. The two or more WTH transforms may be performed simultaneously due to the configuration of the hardware, which may reduce a time duration for image processing when compared to 2D deconvolution. The WTH transforms may be a 1D WTH transform when applied to 1D image data, or a 2D WTH transform when applied to 2D image data. Further, a 2D WTH transform may be decomposed into two 1D WTH transforms when applied to 2D image data.

In some embodiments, the input image I may be the input image data and the opening operation $\circ$ may be an erosion followed by a dilation of the input image. The extracted image component $WTH_i$ may be extracted using a structure element $SE_i$ with the size of i. The structure element $SE_i$ may be differently sized and have different geometries. The structure element $SE_i$ may be sized based on a number of pixels within the structure element SEi. For example, a structure element $SE_3$ may be 2D kernel applied to 2D WTH transforms, wherein i=3 includes a 3×3 pixel array and a structure element $SE_{21}$ wherein i=21 includes 21×21 pixel array. It may be noted that the number, i, may strictly be an odd number for an unambiguous definition of a center of the structure element.

With regards to having different geometries for 2D structure elements, in one embodiment, the structure element $SE_i$ may be a flat or non-flat structure element. In another embodiment, the structure element $SE_i$ may be an approximated circular structure element or square structure element. In some embodiments, the square structure element may reduce computation time due to having the same dimensions in an x-direction and y-direction. More specifically, a 2D WTH transform may be separately decomposed, meaning a 2D WTH transform result may be achieved by performing 1D WTH transforms in the x-direction and y-direction. By separately decomposing the 2D WTH transform, a 2D WTH transformation result may be achieved with reduced computational expense and computation time.

However, the circular structure element for 2D applications may be more compatible with common biological samples, such as cells. Since the circular structure element may be approximated by a staircase circumference, which may then be decomposed into smaller structure elements, computation may be optimized based on the specific computation hardware. Regardless of the size and geometry of the structure element, the WTH transformations of the input image are compatible with GPU processing and may be performed in parallel, which may result in acceptable image processing times (e.g., a fraction of a second). Due to the shorter processing times, after selection of the sizes of the structure elements, image processing according to the method 300 may be automated and may not rely on intervention from a user to generate final images with increased image quality and resolution.

When performing a 1D WTH transform on 1D image data (e.g., a row of pixels in one dimension), the equation 1 may be applied with a 1D structure element (e.g., a number of pixels). In examples wherein the image data is 1D, the structure element may have a size but not geometry due to the one dimensional nature of the image data.

It may be understood that the examples provided for the various aspects of the structure element $SE_i$ are not meant to limit the scope of the present disclosure. The sizes and geometries of the structure element $SE_i$ may deviate from the examples provided without departing from the scope of the present disclosure. By performing the white top-hat transform on the input image, an image may be generated that includes extracted image components $WTH_i$.

As one example of performing the white top-hat transform on the input image data, a plurality of white top-hat transforms may be performed on the same input image data as shown above with regards to FIG. 2 to generate a plurality of WTH transformed images with extracted image components. The plurality of white top-hat WTH transforms may include a first WTH transform, a second WTH transform, and a third WTH transform that may be performed on the first input image to generate a first WTH transformed image with extracted image components, a second WTH transformed image with extracted image components, and a third WTH transformed image with extracted image components, respectively.

The first white top-hat transform may be performed with a first structure element of a first size, the second white top-hat transform may be performed with a second structure element of a second size, and a third white top-hat transform may be performed with a third structure element of a third size. The first size of the first structure element is smaller than the second size of the second structure element. The second size of the second structure element is smaller than the third size of the third structure element. The first size of the first structure element is smaller than the third size of the third structure element. In other words, the first structure element is the smallest, the third structure element is the largest, and the second structure element is an intermediate size between the first structure element and the third structure element.

According to the Nyquist theorem, the smallest features (or highest frequency component) in the image may be twice the size of the pixel. In other words, the WTH transform extracts image features smaller than the size of the structure element, similar in shape to the structure element (for 2D WTH transforms), and brighter than the surrounding. Since biological samples may be the subject of the input image, a suitable candidate to extract high frequency features of a 2D input image into the first WTH transform may be a circular first structure element with a first size of 3 pixels (e.g., 3×3 pixels).

However, the first structure feature with the first size of 3 pixels may not be suitable when magnification of the optical system is large enough that the PSF becomes larger and/or a signal-to-noise ratio of the image is poor and a larger structure element may be selected to avoid noise amplification. With regards to the third WTH transform, the third size of the third structure element may be selected based on the largest size of the desired image feature of a biological sample to be included in the final image (e.g., the morphology-based recomposition). Features larger than the largest structure element may be severely attenuated in the final image. The second size of the second structure element may be selected based on secondary features that a user identifies as relevant.

In other embodiments, the plurality of white top-hat transforms may include fewer or additional white top-hat transforms on the same input image. In particular, at least two white top-hat transforms may be performed on the same input image. In embodiments wherein additional white top-hat transforms are performed, an increase in image quality such as resolution or contrast may occur at the expense of additional computational costs and introducing complexity.

At 308, the method 300 includes generating orthogonalized layers using the transformed image data. The transformed image data may include two or more WTH transformed images with extracted image components acquired with the plurality of white top-hat transforms. Two or more orthogonalized layers may be generated based on the two or more WTH transformed images with extracted image components. In particular, the two or more WTH transformed images with extracted image components may be subtracted from one another in a specific manner to generate the two or more orthogonalized layers. The two or more orthogonalized layers are linearly independent and not related to each other. Generation of two or more 2D orthogonalized layers is illustrated in FIG. 5A-5C. Two or more 1D orthogonalized layers may be generated when applying 1D WTH transform to 1D input image data.

Returning to the example described above wherein two or more white top-hat transforms are performed on the same input image, the two or more WTH transformed images with extracted image components, which includes the first WTH transformed image with extracted image components, the second WTH transformed mage with extracted image components, and the third WTH transformed image with extracted image components, may be used to generate the two or more orthogonalized layers. As described herein, the first WTH transformed image with extracted image components is generated using the smallest structure element size, the second WTH transformed image with extracted image components is generated using the intermediate structure element size, and the third WTH transformed image with extracted image components is generated using the largest structure element size.

A first orthogonalized layer may be the first WTH transformed image with extracted image components, which may be a top layer. A second orthogonalized layer may be the difference between the second WTH transformed image with extracted image components and the first WTH transformed image with extracted image components, which may be an intermediate layer. A third orthogonalized layer may be the difference between the third WTH transformed image with extracted image components and the second WTH transformed image with extracted image components, which may be a base layer.

At 310, the method 300 includes performing additional image processing on the generated orthogonalized layers. The additional image processing may be applied to the two or more orthogonalized layers independently. In other words, each orthogonalized layer may be processed independently due to various image content present in each orthogonalized layer. For example, the first orthogonalized layer may include noise that affects image resolution and image quality. A denoising algorithm may be applied to the first orthogonalized layer. In particular, the denoising algorithm may adjust the contribution of the first orthogonalized layer (e.g., top layer) relative to a combination of the second orthogonalized layer and third orthogonalized layer (e.g., the middle or intermediate layer and the base layer).

As one example, the first orthogonalized layer may be denoised according to equation 2:

$$L1_w = L1\frac{(L1 + l2)}{\max(L1 + L2)} \tag{2}$$

where L1 is the first orthogonalized layer (or top layer), L2 is the second orthogonalized layer (or middle layer), L3 is the third orthogonalized layer (or base layer), $L1_w$ is a weighted first orthogonalized layer (or weighted top layer), and the max operator takes the maximum intensity of the operand. By applying the intensity-based denoising algorithm of equation 2, noise in the background or low intensity areas of the input image may be attenuated.

In some embodiments, a low pass filtering algorithm, wavelet denoising algorithm, or processing mask-based algorithms may be applied to the first orthogonalized layer to refine the layer and reduce the presence of noise. In other embodiments, the second orthogonalized layer and the third orthogonalized layer may include undesired intensity variation, which may be addressed by applying an intensity filtering algorithm. In this way, undesired out-of-focus content that may appear in the final image due to the presence of noise or undesired intensity variation may be corrected before generation of the final image. Overall, by performing additional image processing on the orthogonalized layers and addressing the specific factors in each layer that may reduce image quality in the input image, a final image without undesired out-of-focus image content and increased image resolution and image quality may be generated.

At 312, the method 300 includes calculating scaling factors of the generated orthogonalized layers. Each scaling factor of the generated orthogonalized layers may be applied to the generated orthogonalized layers to weight each layer accordingly in order to increase spatial resolution of the final image (e.g., the morphology-based recomposition). The scaling factors may be determined based on the approximated PSF. For example, an intensity distribution of an object and PSF of the optical system may follow a Gaussian distribution with a specified standard deviation. The Gaussian function is shown in the following equation 3:

$$G(d, s) = \exp\left(\frac{-d^2}{2 \cdot s^2}\right) \tag{3}$$

where s is a standard deviation and d is a size of a structure element. As such, d may be $R_1$ or $R_2$ and s may be $\sigma_1$ or $\sigma_2$ described below.

The scaling factor between two generated orthogonalized layers may be determined according to the following equation 4:

$$\frac{L1}{L2} = \frac{\overline{L1S1}/\overline{L2S1}}{\overline{L1S2}/\overline{L2S2}} \tag{4}$$

where $$\overline{L1S1} = 1 - G(R_1, \sigma_1),$$

$$\overline{L2S1} = 1 - G(R_2, \sigma_1) - \overline{L1S1},$$

$$\overline{L1S2} = 1 - G(R_1, \sigma_2),$$

$$\overline{L2S2} = 1 - G(R_2, \sigma_1) - \overline{L1S2},$$

G is a Gaussian function, $\sigma_1$ is a restored standard deviation, $\sigma_2$ is a blurred standard deviation, $R_1$ is a half size of the structure element of a first layer ($L_1$), and $R_2$ is a half size of the structure element of a second layer ($L_2$). For example, for a structure element of a 3×3 array, the half size of the corresponding layer (e.g., $R_1$ or $R_2$) may be equal to 1. The restored standard deviation is the standard deviation of the targeted point spread function and the blurred standard deviation is a standard deviation of the acquired image data. Scaling the two or more pairs of orthogonalized layers according to equation 4 enables each orthogonalized layer to contribute appropriately to the final image based on an ability of each orthogonalized layer to increase image resolution, reduce the presence of undesired intensity such as out-of-focus content, and increase overall image quality.

Equation 4 may be applied to the plurality of orthogonalized layers, including the first orthogonalized layer, the second orthogonalized layer, and the third orthogonalized layer, generated from the two or more WTH transformed images with extracted image components in the example described above. A first scaling factor between the first orthogonalized layer and the second orthogonalized layer may be calculated with equation 4. $L_1$ may refer to the first orthogonalized layer and $L_2$ may refer to the second orthogonalized layer.

It may be understood, that a ground truth image refers to an image without blurring and/or out-of-focus image content that is introduced when an acquired image is captured by the imaging optical system. Blurring and out-of-focus image content is present in the acquired image. Since the smallest size of the feature structure may be twice the image pixel size, and an intensity distribution of a smallest object (e.g., ground truth) in a roughly critically sampled input image, it may be assumed that a ground truth PSF of the ground truth image is a Gaussian curve with a standard deviation of $\sigma_1$=1 pixel and a full width at half maximum (FWHM) of approximately 2.4 pixels. As described above, the acquired image may include blurring and out-of-focus content introduced by the imaging system. Accordingly, the PSF of the imaging optical system may also be approximated by a Gaussian function with a standard deviation of 2 pixels or using other analytical functions. When the PSF of the imaging optical system is approximated as described above, a resulting imaged object (e.g., a blurred object) may have a PSF of a Gaussian distribution with a blurred standard deviation (e.g. $\sigma_2$=2 pixels).

Additionally, a second scaling factor between the second orthogonalized layer and the third orthogonalized layer may also be calculated with equation 4. In this case, $L_1$ may refer to the second orthogonalized layer and $L_2$ may refer to the third orthogonalized layer. Since the second orthogonalized layer and the third orthogonalized layer capture larger features of the input image, the size of the standard deviation of the Gaussian function of the intensity distribution for the second orthogonalized layer and the third orthogonalized layer may be more than 10 pixels, resulting in a reduced blurring effect by the PSF of the optical system, which has a PSF with a standard deviation, $\sigma=2$. As such, the restored standard deviation $\sigma_1$ and the blurred standard deviation $\sigma_2$ may be similar in value, causing the second scaling factor between the second orthogonalized layer and the third orthogonalized layer to be reduced to close to 1 (e.g., between 1 and 2).

As structure size in the input image increases, the advantages of resolution restoration are reduced since the blurring effect was reduced in the first place. In fact, when the scaling factor between two adjacent orthogonalized layers (e.g., the first and second orthogonalized layers or the second and third orthogonalized layers) is equal to 1, one of the two adjacent layers may be included in the morphology-based recomposition process since there is no benefit of using additional orthogonalized layers. The first scaling factor between the first orthogonalized layer (e.g., top layer) and the second orthogonalized layer (intermediate layer) is likely to be much greater than unity (e.g., greater than 2), which is generally true for the top layer and middle layers.

As such, the first orthogonalized layer (or the top layer) and the second orthogonalized layer (or the intermediate layer) contribute significantly to the process of increasing in resolution. In contrast, the second orthogonalized layer (or the intermediate layer) and third orthogonalized layer (or the base layer) do not contribute significantly to the increase in resolution compared to the first orthogonalized layer and the second orthogonalized layer. Since the middle layer and base layer do not contribute significantly to the increase in resolution comparatively, including more than three layers or additional intermediate layers (or middle layers) in the morphology-based recomposition becomes less effective and even redundant.

In the example provided above, the estimated PSF of the optical system follows a Gaussian distribution. In some embodiments, the estimated PSF of the optical system may follow other types of distributions, including a Lorentzian distribution or a Moffat distribution. As such, equation 2 may be adjusted accordingly to incorporate the appropriate distribution to achieve a desired resolution restoration of the input image. In other embodiments, the estimated PSF may be widened due to the presence of excessive noise in the input image. To reduce the presence of noise, the scaling factor (e.g., the first scaling factor or the second scaling factor) may be reduced accordingly.

At 314, the method 300 includes composing final image data by applying the scaling factors to the generated orthogonalized layers. In particular, the final image may be generated by applying one or more scaling factors to one or more pairs of adjacent orthogonalized layers to generate the final image. As described herein, the pair of adjacent orthogonalized layers comprise one of the top layer and the base layer, the top layer and one of the one or more intermediate layers, two intermediate layers of the one or more intermediate layers, and one of the one or more intermediate layers and the base layer. Applying the scaling factors to compose the final image may include multiplying one orthogonalized layer of the pair of adjacent orthogonalized layers by a respective scaling factor for each pair of adjacent orthogonalized layers, and adding each scaled orthogonalized layer and non-scaled orthogonalized layer together. As mentioned herein, the scaling factor is applied to an upper orthogonalized layer of the pair of adjacent orthogonalized layers.

As an example, a first pair of adjacent orthogonalized layers may include the first orthogonalized layer and the second orthogonalized layer and a second pair of adjacent orthogonalized layers may include the second orthogonalized layer and the third orthogonalized layer. Since the first orthogonalized layer is an upper orthogonalized layer of the first pair and the second orthogonalized layer is an upper orthogonalized layer of the second pair, a first scaling factor is applied to the first orthogonalized layer and a second scaling factor is applied to the second orthogonalized layer. Applying the first scaling factor and the second scaling factor may include summing a product of the first orthogonalized layer and the first scaling factor, a product of the second orthogonalized layer and the second scaling factor, and the third orthogonalized layer to generate the final image. In this way, the final image may be composed by multiplying the first scaling factor and the first orthogonalized layer to generate a scaled first orthogonalized image, multiplying the second scaling factor and the second orthogonalized layer to generate a scaled second orthogonalized, and adding the scaled first orthogonalized image, the scaled second orthogonalized image, and the third orthogonalized image (e.g., a non-scaled third orthogonalized image) together.

At 316, the method 300 includes displaying a final image with a display device and/or storing the final image in memory. The final image may be displayed using a display device, such as a display device communicatively coupled to a computing system, which may be the computing system 124 of FIG. 1. In this way, a user may visually evaluate the content of the final image. By restoring resolution of image and increasing image quality, the user may identify features of interest within the final image more easily. Further, the reconstructed image may be stored in memory of the computing system (e.g., memory 128 of FIG. 1) or in an image archive such as a picture archive and communication system to enable a user to access the final image at a later time. The method 300 then ends.

It may be understood that the method 300 is exemplary and a process for generating the morphology-based recomposition may differ without departing from the scope of the present disclosure. For example, the additional image processing may be optional depending on an initial image quality of the input image.

Figure 4B:
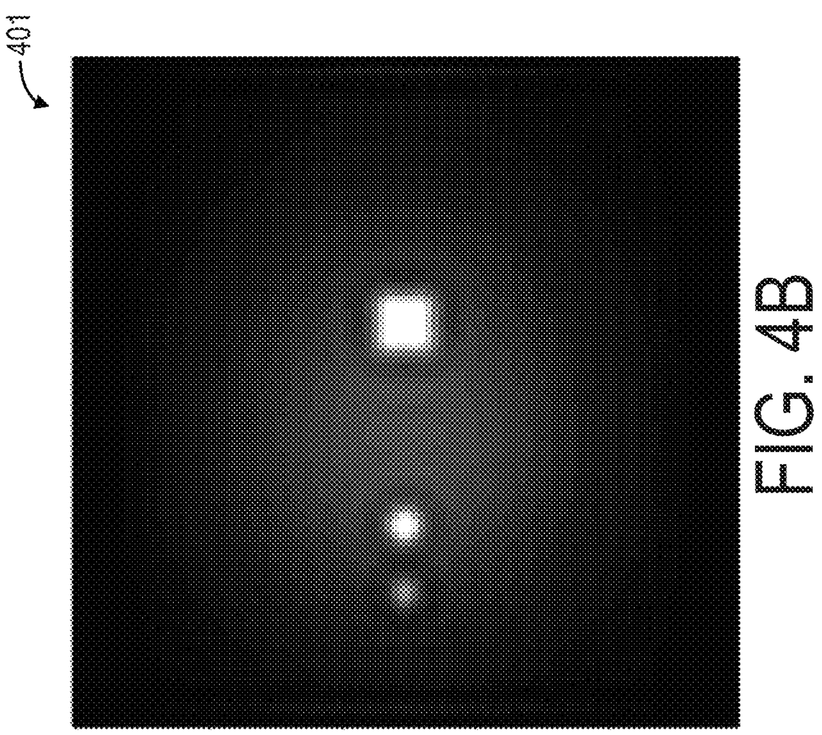
FIGS. 4A-4F show examples of a 2-dimensional (2D) phantom image, examples of final 2D images, and examples of 2D white top hat (WTH) transformations of the phantom image.
Figure 4A:
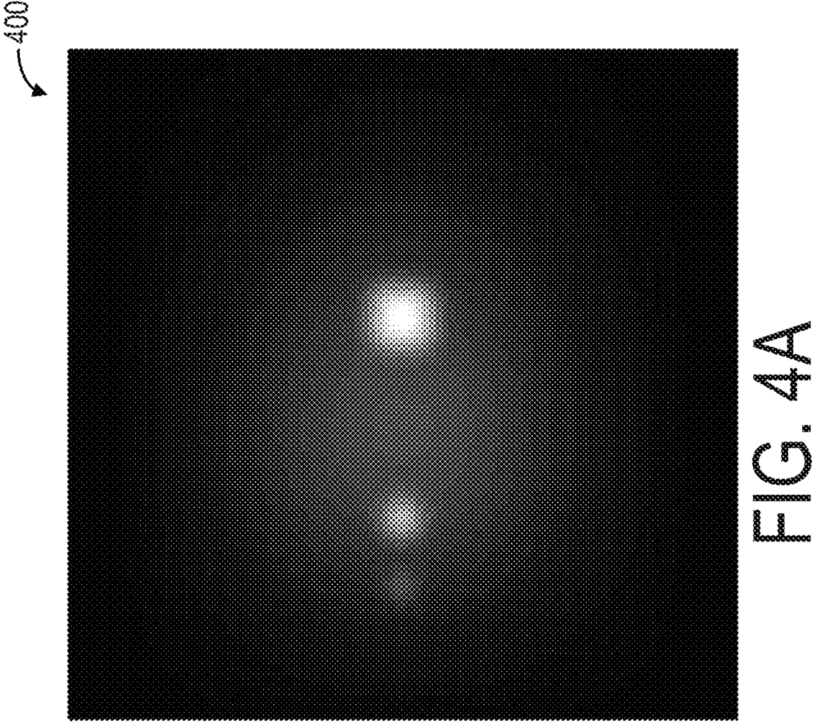

FIG. 4A shows a 2D input image 400 wherein a plurality of white top hat (WTH) transforms are applied to the input image. The input image 400 is a 100×100 pixel image simulated with a digital phantom, the digital phantom includes a 2×2 white pixel square, 4×4 pixel square, and 8×8 pixel square. All normalized intensities of the pixels in the square is one, and the background is zero. The input image 400 is computed based on an optical system with a blurring point spread function in a Gaussian distribution with a standard deviation of two pixels. The input image 400 also includes a diffusive background, which is a Gaussian distribution with a standard deviation of 20 pixels and peak intensity of 0.1, is superimposed as the background intensity variation. In addition, an additive Poisson noise was applied.

FIG. 4B is an image 401 of a product of a 2D deconvolution treatment wherein a dark halo surrounds the bright squares. FIG. 4C is a final image 402 generated according to the embodiment described herein, wherein the final image is composed from two or more orthogonalized layers that are scaled using a respective scaling ratio. When compared with input image 400, the square included in final image 402 exhibits higher contrast, increased resolution, and the background intensity is effectively reduced without the presence of a dark halo (as seen in image 401).

Figure 4D:
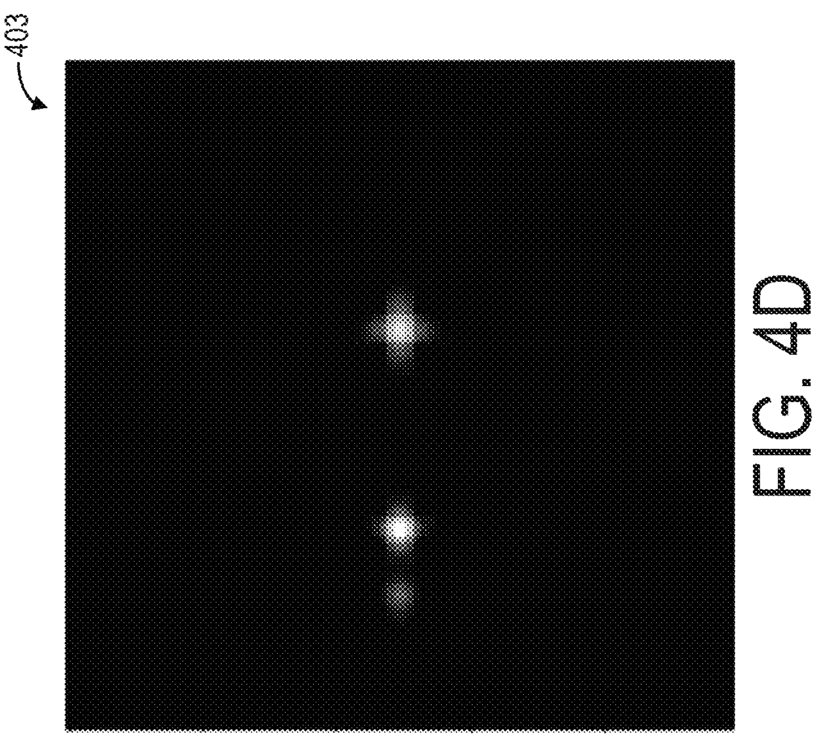
Figure 4C:
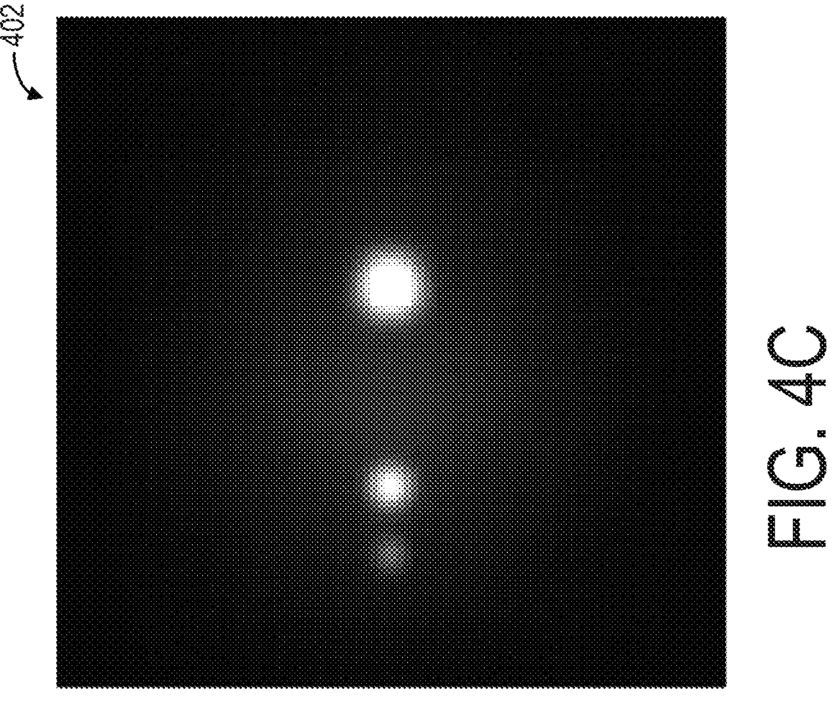
Figure 4F:
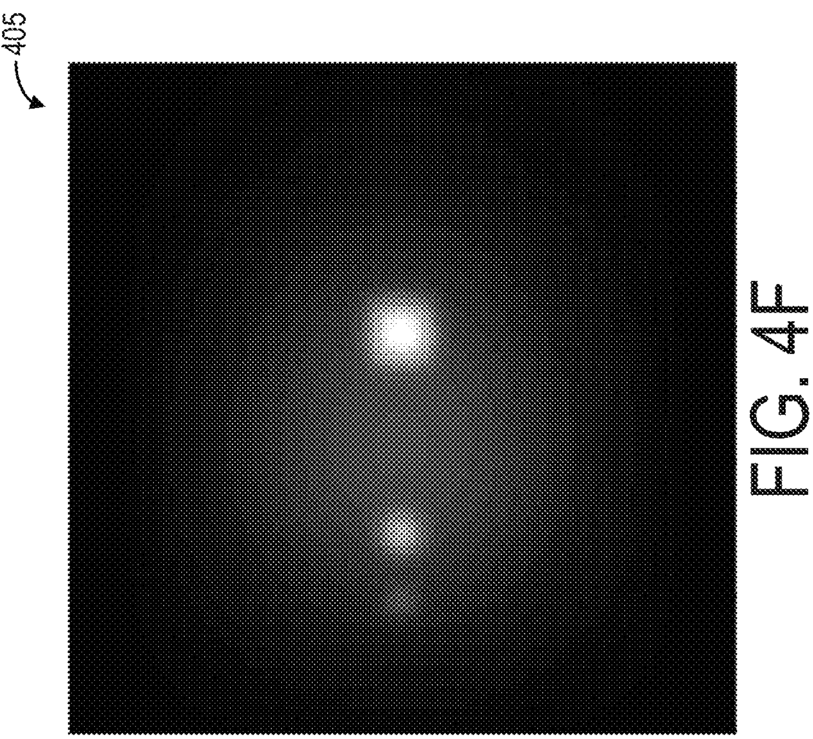
Figure 4E:
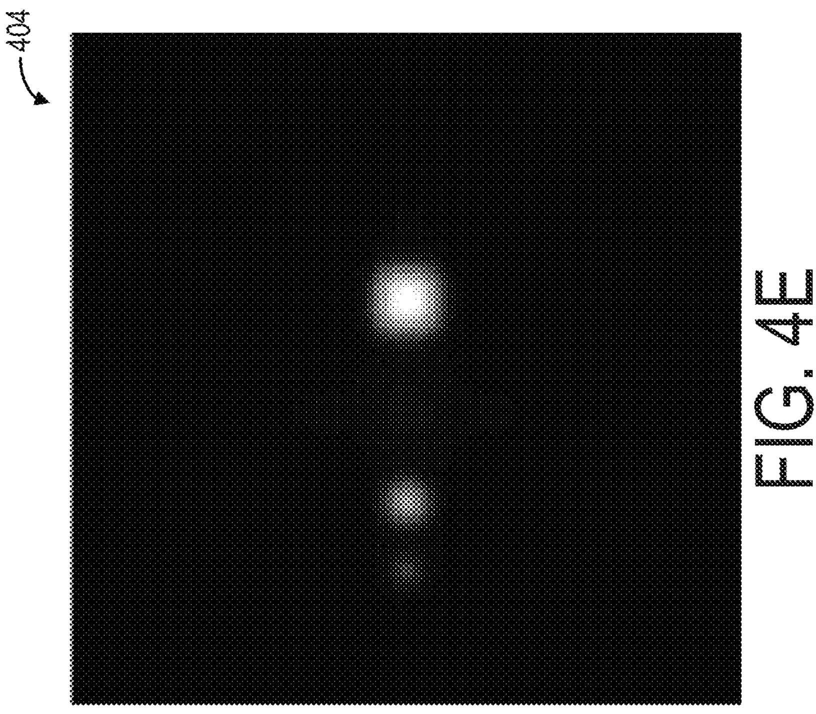

FIGS. 4D, 4E, and 4F show a plurality of white top hat transformed images, including first white top hat (WTH) transformed image 403, a second WTH transformed image 404, and a third WTH transformed image 405, generated with a plurality of white top-hat (WTH) transforms. The plurality of WTH transforms may be performed according to the method described above with regards to FIG. 3. Similarly, the WTH transformed images may be used to generate the two or more orthogonalized layers wherein the final image 402 is composed thereof. The plurality of WTH transforms may include a first WTH transform, a second WTH transform, and a third WTH transform that may be applied to the input image 400 to generate the first WTH transformed image 403 with extracted image components, the second WTH transformed image 404 with extracted image components, and the third WTH transformed image 405 with extracted image components, respectively.

The first WTH transformed image 403 is generated by performing the first WTH transform with a first structure element with a size of 3 pixels on the input image 400. The second WTH transformed image 404 is generated by performing the second WTH transform with a second structure element with a size of 9 pixels on the input image 400. The third WTH transformed image 405 may be generated by performing the third WTH transform with a third structure element with a size of 51 pixels on the input image 400. The first structure element, the second structure element, and the third structure element are flat square structure elements. The first structure element is smallest in size, the second structure element is intermediate in size, and the third structure element is largest in size.

The first WTH transformed image 403 includes smaller features compared to the second WTH transformed image 404 and the third WTH transformed image 405. The smallest structure element extracts smaller features of high intensity. In this way, high frequency image components are collected in the first WTH transformed image 403. The second WTH transformed image 404 includes larger features compared to the first WTH transformed image 401 and smaller features compared to the third WTH transformed image 405. Thus, the intermediate structure element extracts larger features of lower intensity than the smallest structure element. The third WTH transformed image 405 includes larger features compared to the first WTH transformed image 403 and the second WTH transformed image 404, and accordingly, the intermediate structure element extracts larger features of lower intensity than the smallest structure element and the intermediate structure element.

FIGS. 5A, 5B, and 5C show a plurality of orthogonalized layers generated based on a plurality of white top hat (WTH) transformed images. The plurality of WTH transformed image may be the plurality of WTH transformed images (e.g., the first WTH transformed image 403, the second WTH transformed image 404, and the third WTH transformed image 405) described above with regards to FIGS. 4D-4F. The plurality of orthogonalized layers may include a first orthogonalized layer 500, a second orthogonalized layer 501, and a third orthogonalized layer 503.

The first orthogonalized layer 500 may be a first WTH transformed image with extracted feature components, such as the first WTH transformed image 403 of FIG. 4D. The second orthogonalized layer 501 may be the difference between a second WTH transformed image (e.g., the second WTH transformed image 404 of FIG. 4E) with extracted image components and the first WTH transformed image with extracted image components. The third orthogonalized layer 503 may be the difference between a third WTH transformed image (e.g., the third WTH transformed image 405 of FIG. 4F) with extracted image components and the second WTH transformed image with extracted image components. The first orthogonalized layer 500 represents intensity of the top layer, the second orthogonalized layer 501 represents intensity of the middle layer, and the third orthogonalized layer 503 represents the base components of the original image.

Figure 5D:
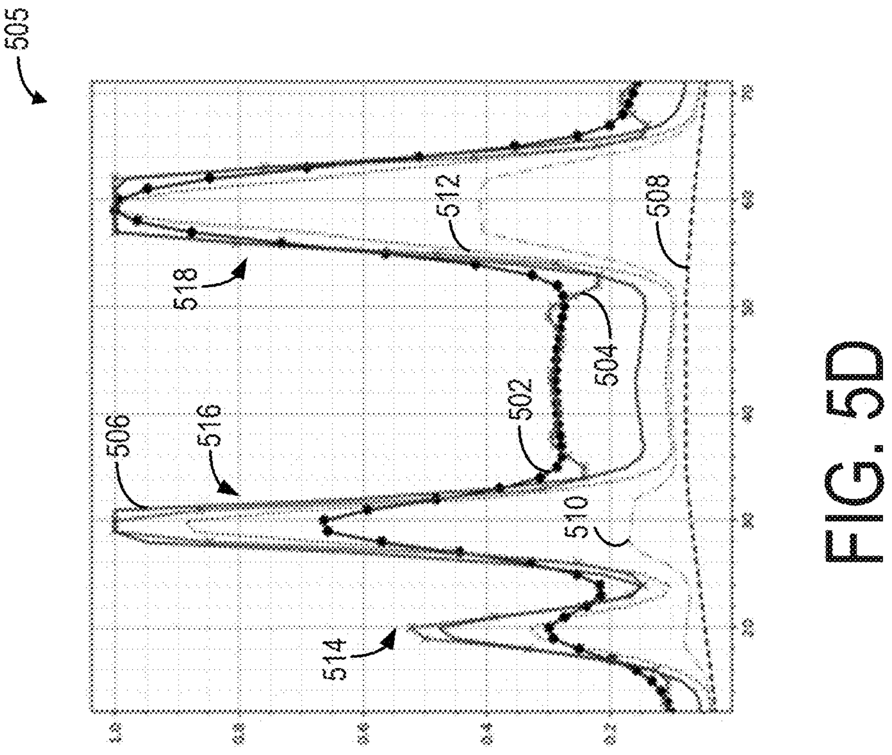
Figure 5C:
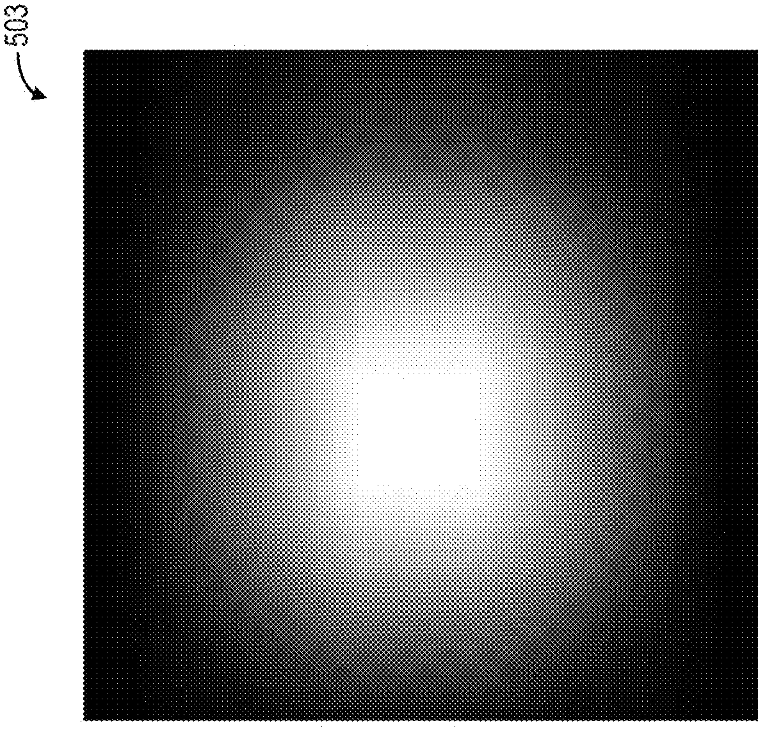

FIG. 5D shows a stacked intensity profile 505 illustrating the contributions of the plurality of orthogonalized layers of a morphology-based recomposition in the image resolution restoration process. The stacked intensity profile 505 is an intensity profile of a pixels along a horizontal row across the middle of the digital phantom (e.g., the 2×2 pixel square, the 4×4 pixel square, and the 8×8 pixel square described above in FIG. 4A). The stacked intensity profile 505 includes first trace 502, a second trace 504, a third trace 506, a fourth trace 508, a fifth trace 510, and a sixth trace 512. Traces may alternatively be referred to as curves.

The first trace 502 (e.g., a connected solid line with large filled circles) represents the intensity of the input image (e.g., input image 400 of FIG. 4A). A first peak 514 at x=20, a second peak 516 at x=30, and a third peak at x=60 of the first trace 502 indicates peak reduction and broadening due to a resolution-degrading PSF of a simulated optical system when compared to an original straight-wall intensity profile with an intensity of one. The second trace 504 represents (e.g., connected solid line with a cross marker) the 2D Richardson-Lucy deconvolution algorithm results after 50 iterations. When compared with the first trace 502, the peak height is increased and peak width is decreased for the first peak 514 and the second peak 516. However, the contrast to the background between the second peak 516 and third peak 518 is reduced (e.g., background intensity between x=35 and x=50 is higher than zero) due to the inability of two-dimensional (2D) deconvolution to remove background intensity variation.

The third trace 506 (e.g., solid line) represents the final image generated according to the embodiments described herein, which is a morphology-based recomposition based on applying a first scaling factor between the first orthogonalized layer 500 and the second orthogonalized layer 501 and a second scaling factor between the second orthogonalized layer 501 and the third orthogonalized layer 503. When compared with the first trace 502, the peak height is increased and peak width is decreased for the first peak 514 and the second peak 516, similar to the second trace 504. However, when compared with the second trace 504, the contrast between the second peak 516 and the third peak 518 is increased, indicating a reduction in background intensity variation between x=35 and x=50.

The fourth trace 508 (e.g., dashed line) represents the contribution of the third orthogonalized layer 503 to the intensity. The fifth trace 510 (e.g., dash-dot line) represents the contribution of second orthogonalized layer 501 and the third orthogonalized layer 503 combined without a scaling factor to the intensity. The sixth trace 512 (e.g., dotted line) represents the contribution of the first orthogonalized layer 500, the second orthogonalized layer 501, and the third orthogonalized layer 503 combined without scaling factors to the intensity. The trace 506 has increased resolution compared to the trace 512 due to the use of scaling factors between layers.

When compared to the fourth trace 508, the sixth trace 512 contributes more significantly to resolution restoration due to the contribution of higher layers. The fourth trace 508 contributes significantly more to background intensity variation than the fifth trace 510 and the sixth trace 512 since the third orthogonalized layer 503 includes the largest image feature components. It may be noted that the background intensity variation may further be reduced when a scaling factor applied to the third orthogonalized layer 503 is reduced to lower than one or even zero.

FIGS. 6A, 6B, 6C, and 6D show an input image 600 (e.g., a 2D image of an image stack), a final image 601 based on a morphology-based recomposition, a deconvolution algorithm result 603, and a stacked intensity profile 605. The input image 600 is an image simulated with a digital phantom, the digital phantom including an HL60 nucleus. The input image 600 is a superposition of a first image wherein a blurring point spread function (PSF) in a Gaussian distribution with a standard deviation of two pixels is applied to the ground truth image and a second image wherein a blurring point spread function (PSF) in a Gaussian distribution with a standard deviation of 20 pixels is applied to the ground truth image. The second image is more attenuated and superimposed onto the first image to simulate the out-of-focus content and Poisson noise is applied to the superposition to generate the simulated input image 600.

The final image 601 (e.g., a morphology-based recomposition result) may be generated with a plurality of orthogonalized layers, which may include a first orthogonalized layer, a second orthogonalized layer, and a third orthogonalized layer. As described herein, for biological samples, the circular structure elements may be more compatible with features of biological subjects. As such, the first orthogonalized layer may be a first WTH transformed image with extracted feature components generated by performing a first WTH transform on the input image with a structure element size of 5 pixels (e.g., circular structure element with size of 5×5). The second orthogonalized layer may be the difference between a second WTH transformed image with extracted image components and the first WTH transformed image with extracted image components. The second WTH transformed image with extracted image components may be generated by performing a second WTH transform on the input image with a structure element size of 21 pixels (e.g., circular structure element with size of 21×21).

The third orthogonalized layer may be the difference between a third WTH transformed image with extracted image components and the second WTH transformed image with extracted image components. The third WTH transformed image with extracted image components may be generated by performing a third WTH transform on the input image with a structure element size of 81 pixels (e.g., circular structure element with size of 81×81). The first orthogonalized layer may represent intensity of the top layer, the second orthogonalized layer may represent intensity of the middle layer, and the third orthogonalized layer may represent the base layer of the input image. An additional denoising algorithm may be applied to the first orthogonalized layer to reduce the additive Poisson noise introduced when generating the input image. More specifically, equation 2 may be applied to the first orthogonalized layer (or top layer).

The deconvolution algorithm result 603 may be a 2-dimensional (2D) Richardson-Lucy (RL) algorithm after 50 iterations. The 2D RL algorithm may be performed according to the following equation:

$$\hat{I}_{k+1} = \hat{I}_k\left(PSF * \frac{I}{PSF \otimes \hat{I}_k}\right) \tag{5}$$

where I may be an input image, such as input image 600, PSF is a blurring point spread function, $\hat{I}_{k+1}$ is a deconvolution result after k iterations, ⊗ is a correlation operator, and ⊗ is a convolution operator.

The deconvolution algorithm result 603 shows sharper image feature details and restored intensity. However, the 2D RL algorithm fails to remove the background intensity variation due to the algorithms inability to remove the simulated out-of-focus emission. Further, the deconvolution algorithm result 603 exhibits undesired out-of-focus content, such as poor contrast in addition to a "white halo" due to noise amplification around the bright objects, when compared to the final image 601 (or morphology-based recomposition). The undesired out-of-focus content in the 2D RL result may not be reduced (e.g., by reducing a number of iterations of the RL algorithm) without affecting a quality of the resolution restoration.

Figure 6B:
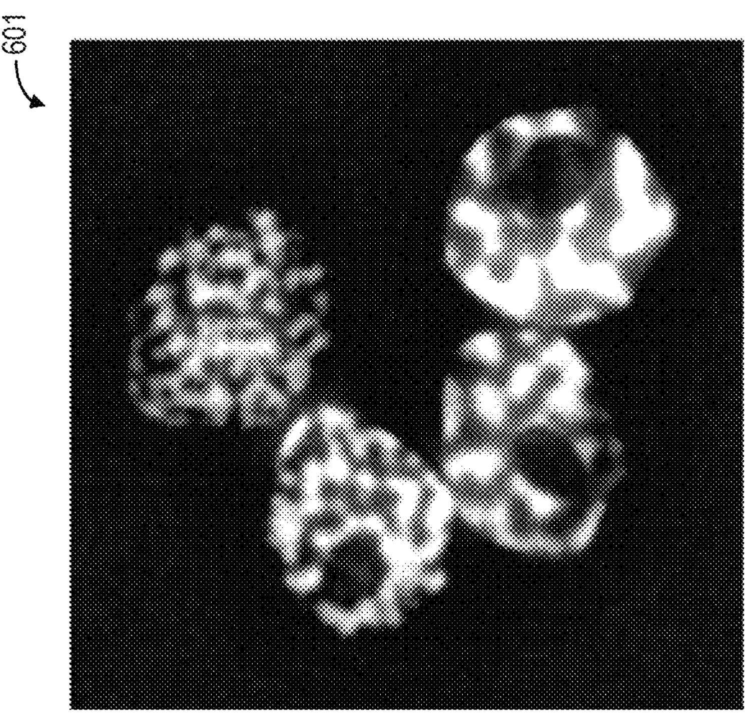
FIGS. 6A-6D show a second example of implementing a morphology-based recomposition using a 2D phantom image.
Figure 6A:
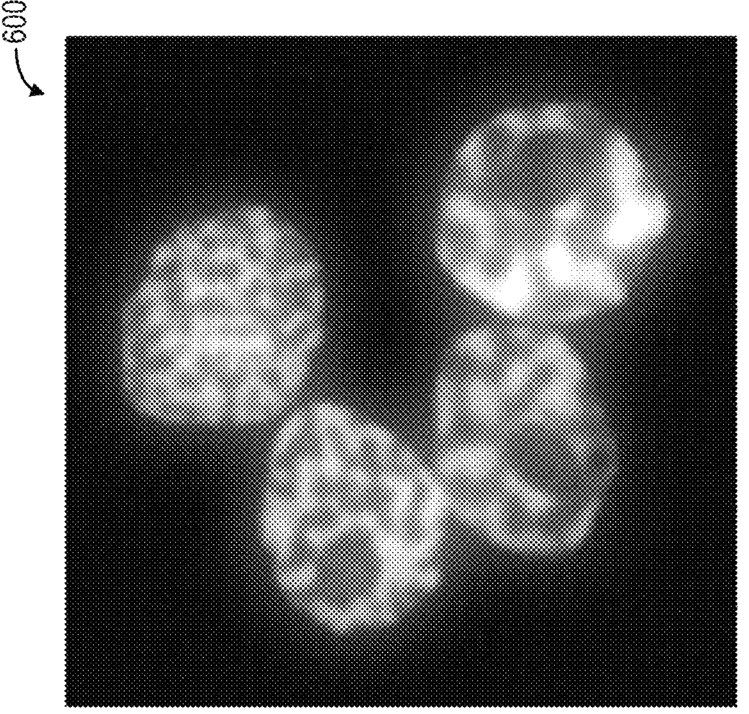
Figure 6D:
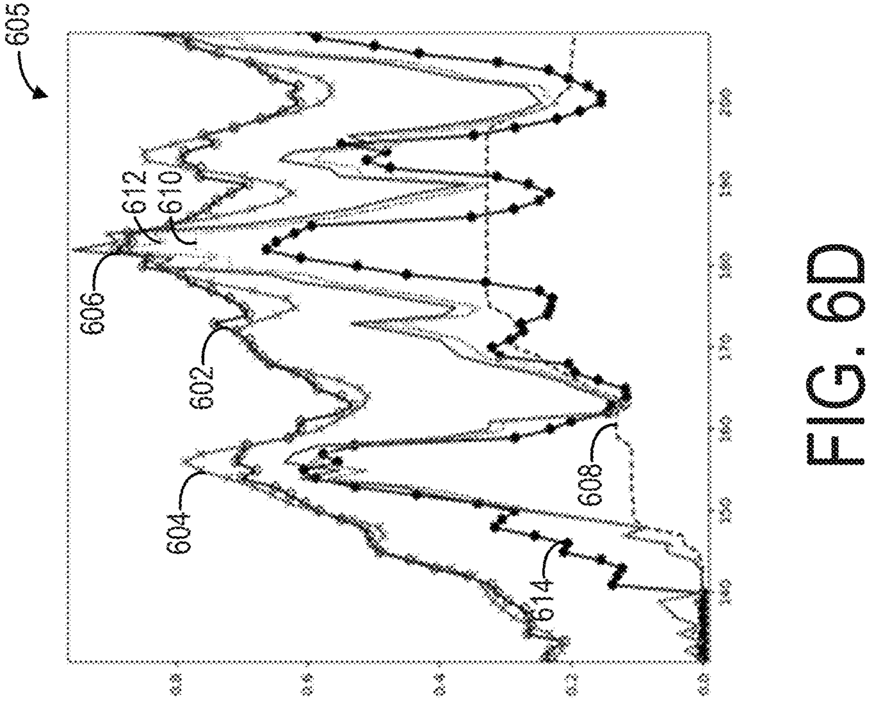
Figure 6C:
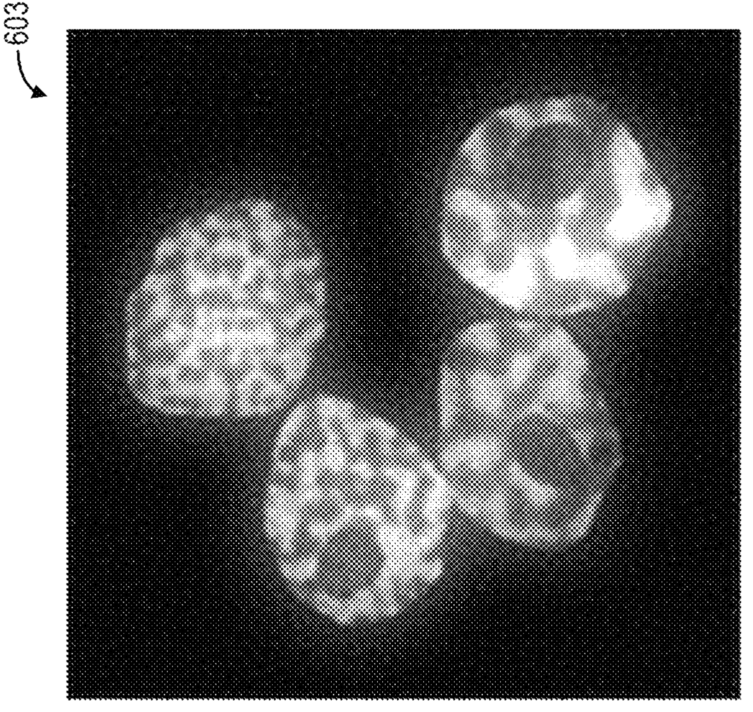

FIG. 6D shows a stacked intensity profile 605 illustrating the contributions of the plurality of orthogonalized layers of a morphology-based recomposition in the image resolution restoration process. The stacked intensity profile 605 includes a first trace 602, a second trace 604, a third trace 606, a fourth trace 608, a fifth trace 610, a sixth trace 612, and a seventh trace 614.

The first trace 602 (e.g., a connected scatter plot with large open dots) represents the intensity of the input image 600. The second trace 604 (e.g., a solid line with a cross marker) represents the deconvolution algorithm results after 50 iterations. The third trace 606 (e.g., solid line) represents the final image 601, which is a morphology-based recomposition based on applying a first scaling factor between the first orthogonalized layer and the second orthogonalized layer and a second scaling factor between the second orthogonalized layer and the third orthogonalized layer.

The fourth trace 608 (e.g., dashed line) represents the contribution of the third orthogonalized layer to the intensity. The fifth trace 610 (e.g., dash-dot line) represents the contribution of the combination of the second and the third orthogonalized layers to the intensity. The sixth trace 612 (e.g., dotted line) represents the contribution of the combination of the first, the second, and the third orthogonalized layers to the intensity. The seventh trace 614 (a solid line with filled circles) represents the intensity of the ground truth image. When compared to the first trace 602 (e.g., the input image 600) and the second trace 604 (e.g., deconvolution algorithm result 603), the third trace 606 includes removed background intensity and a full-width-at-half-maximum (FWHM) are reduced, indicating an increase in resolution in the final image 601.

The morphology-based recomposition methods described above (e.g., process 200 and method 300 of FIGS. 2 and 3, respectively) are discussed with example 2D images (e.g., described in regards to FIGS. 4A-6D). However, the 2D morphology-based recomposition methods may also be applied to a 3D image dataset (e.g., an image stack) by implementing the methods with each 2D image in a stack of 2D images to enhance resolution in all three dimensions (e.g. along the x-axis, the y-axis, and the z-axis) of the 3D image dataset. Additional 1D morphology-based recomposition can also be applied along the third axis (e.g. Z-axis) to further enhance the resolution in z-direction.

Figures 7A, 7B:
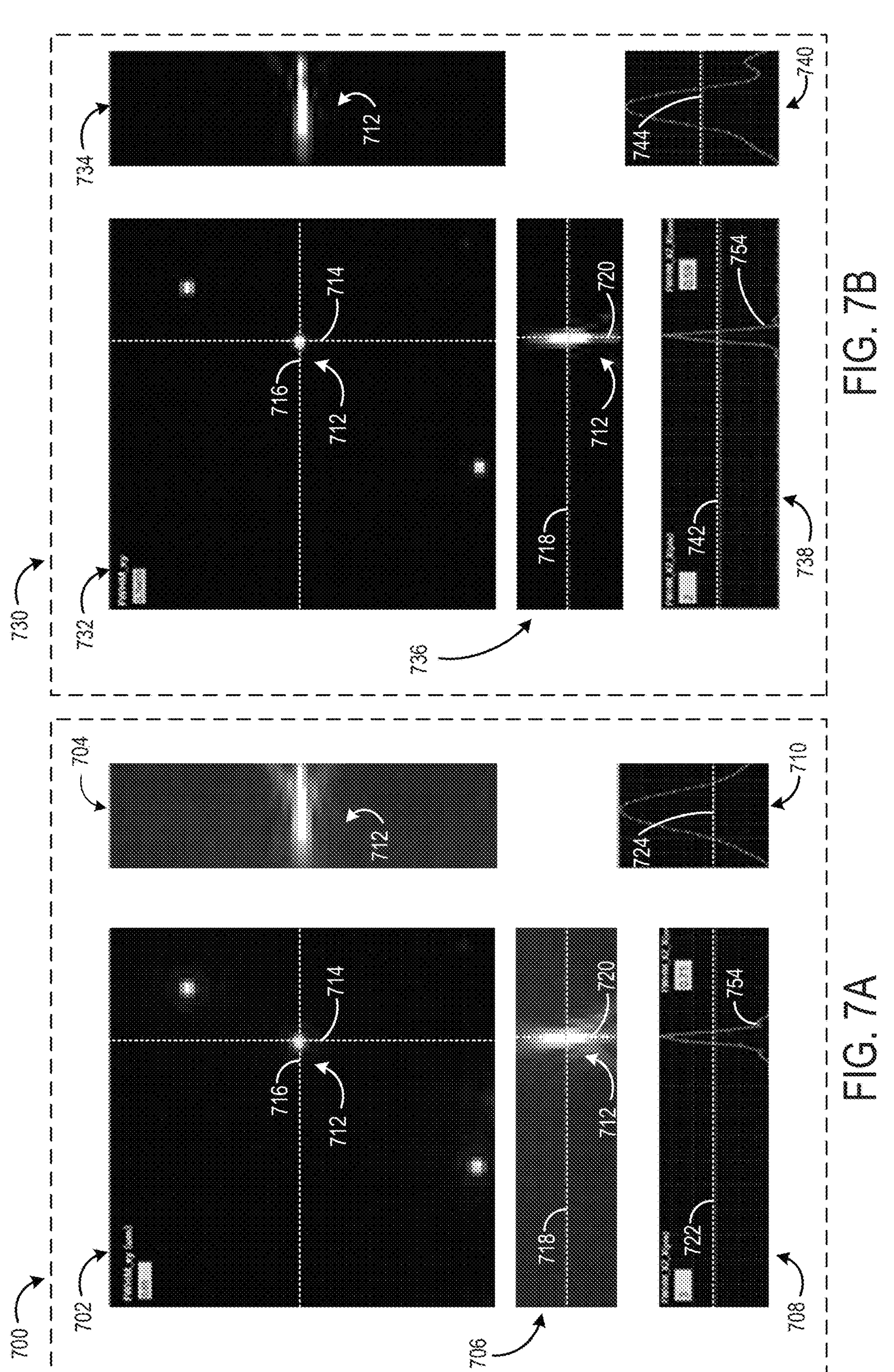
FIGS. 7A-7E show a first example of implementing morphology-based recomposition using a 3-dimensional (3D) image dataset.

FIG. 7A shows 3D image dataset 700 comprising an input image stack of a plurality of 2D images. Each of the 2D images is a 100×100 pixel image in an x-y plane. The z-axis may be a stacking axis along which the 2D images are stacked. The 3D image dataset 700 includes 40 z-positions (e.g., 40 2D images) with a z-step size of 0.25 μm, however, a number of 2D images in an image stack may be greater or fewer and/or a z-step size may be larger or smaller without departing from the scope of the present disclosure. The 3D image dataset 700 is of three beads, including a bead of interest 712, wherein each bead is a sphere.

The 3D image dataset 700 is shown in an xy view 702, a yz view 704, and an xz view 706, wherein the yz view 704 is a section taken along a first axis 714, and the xz view 706 is a section taken along a second axis 716. As used herein, an "xy view" is a view of image data in an xy-plane, a "yz view" is a view of image data in a yz-plane, and an "xz view" is a view of image data in an xz-plane, wherein the xy view, the yz view, and the xz view are perpendicular to one another. As shown in the yz view 704 and the xz view 706, a characteristic non-isotropic PSF image is elongated along the z-axis (e.g., optical axis) due to spherical aberration, resulting in a distorted representation of the spherical bead of interest 712 in the 3D image dataset 700. The bead of interest 712 has an estimated FWHM of 0.65 μm in the xy direction approximated by fitting the pixel values (e.g., intensity) in the xy view 702 to a 2D Gaussian model.

An x-direction intensity plot 708 shows an intensity along a third axis 718 (e.g., z=20), and a z-direction intensity plot 710 shows an intensity along a fourth axis 720 (e.g., x=55). The x-direction intensity plot 708 includes a fifth axis 722 and the z-direction intensity plot 710 includes a sixth axis 724, wherein the fifth axis 722 and the sixth axis 724 mark half of the maximum peak intensity for the purposes of visually showing the FWHM of the intensity peaks in the respective intensity plots (e.g., width of the peaks along the fifth axis 722 and the sixth axis 724). The FHWM along the z-axis is 4.9 μm as shown in the z-direction intensity plot 710, which is correlated to the z-resolution. The FHWM in the z-direction of 4.9 μm being greater than the estimated FWHM in the xy plane of 0.65 μm is further evidence of PSF elongation in the z-direction. Additionally, the FWHM along the x-axis is 0.71 μm, as shown in the x-direction intensity plot 708, is also greater than the estimated FWHM of 0.65 μm, which may be due to displacement of the fifth axis 722 away from focus.

FIG. 7B shows 3D image dataset 730, wherein the 3D image dataset 730 results from applying 2D morphology-based recomposition to each 2D image in the 3D image dataset 700 (e.g., forty 2D images with z-step size 0.25 μm). The 3D image dataset 730 is shown in an xy view 732, a yz view 734, and an xz view 736, wherein the yz view 734 is a section taken along the first axis 714 and the xz view 736 is a section taken along the second axis 716.

An x-direction intensity plot 738 with a seventh axis 742 marking half maximum of the peak shows that the FWHM in the x-direction is reduced to 0.59 μm (from 0.71 μm in the x-direction intensity plot 708 of FIG. 7A). Such a reduction is expected following a 2D morphology-based recomposition (e.g., in the x and y dimensions), as described above with regards to FIGS. 4A-6D.

Further, a z-direction intensity plot 740 with an eighth axis 744 marking half maximum intensity shows the FWHM in the z-direction reduced to 3.5 μm (from 4.9 μm in the z-direction intensity plot 710 of FIG. 7A). Thus, 2D morphology-based recomposition both increases on-focus resolution and reduces out-of-plane emission, thereby further increasing image contrast and increasing z-resolution.

Figure 7D:
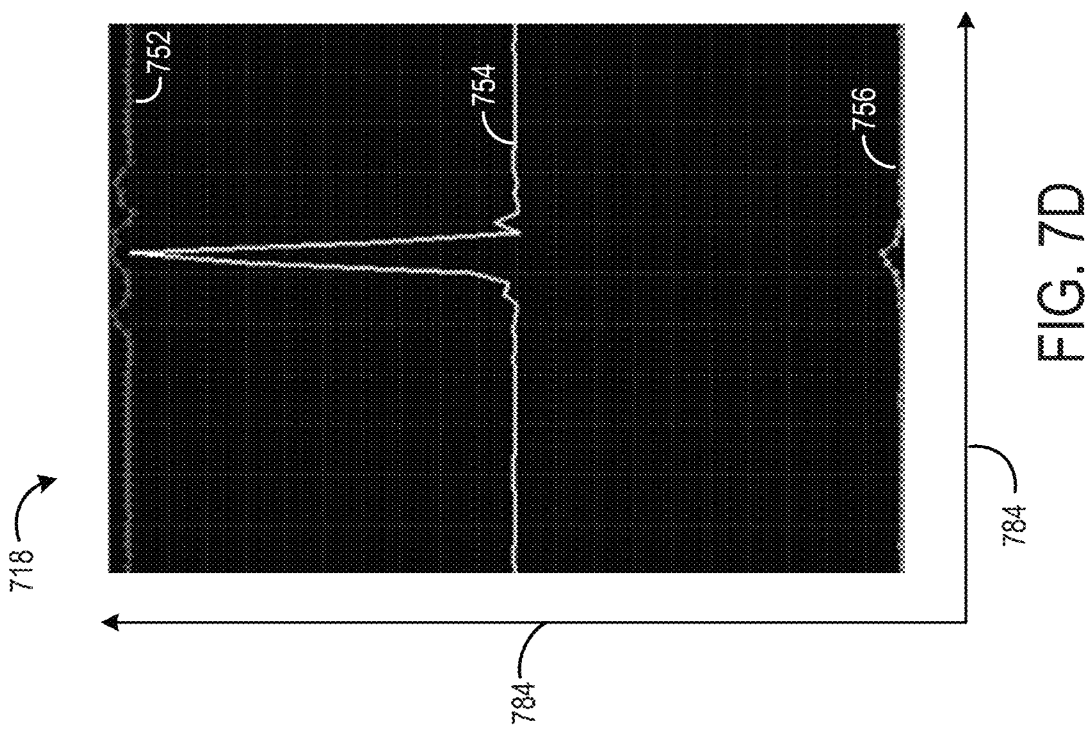
Figure 7C:
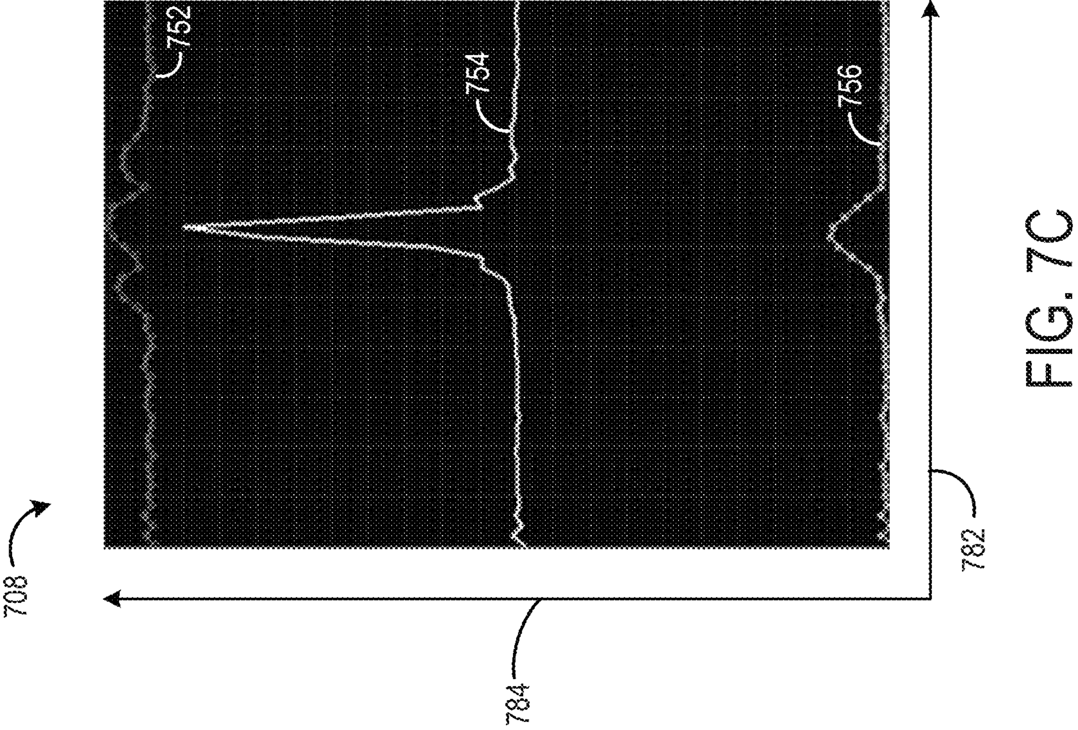

Reduced out-of-plane emission due to 2D morphology-based recomposition performed on each 2D image in the image stack is further evinced in comparing the intensity plots 708 and 738 reproduced in FIGS. 7C and 7D, respectively. The intensity plots 708 and 738 show intensity (e.g., increasing along the direction indicated by vertical arrow 784) along an x-direction (e.g., increasing along the direction indicated by horizontal arrow 782) and each include a first trace 752 showing intensity along the x-direction at z=0 (e.g., in the top 2D image), a second trace 754 showing intensity along the x-direction at z=20 (e.g., in a middle 2D image), and a third trace 756 showing intensity along the x-direction at z=40 (e.g., in the bottom 2D image). As described above, the intensity peak of the second trace 754 has a smaller FWHM in the x-direction intensity plot 738 than the x-direction intensity plot 708, thus resolution is increased along the x-direction by 2D morphology-based recomposition in the x- and y-dimensions. Further, the intensities of the first trace 752 and the third trace 756 are reduced in the plot 738 compared to the plot 708. Thus, out-of-focus emission is reduced by applying 2D morphology-based recomposition to each 2D image in a 3D image dataset comprising a stack of 2D images. A step size along the z-axis between focal planes of the 2D images of the 3D image dataset may be uniform or non-uniform when applying 2D morphology-based recomposition perpendicularly to the z-axis. Therefore, the morphology-based recomposition methods disclosed herein may allow flexibility to improve the resolution along the stacking axis for 3D image datasets obtained by imaging systems with varying precision of focal plane step sizes.

To further enhance resolution of the image stack along the stacking axis (e.g., z-axis), 3D morphology-based recomposition may be performed on the image stack. For example, 3D morphology-based recomposition may comprise performing an additional 1D morphology-based recomposition (e.g., along the z-axis) after 2D morphology-based recomposition is completed for each 2D image in the image stack (e.g., where the 2D images are in x-y planes with a z-step size therebetween). A method 1000 is shown in FIG. 10A for 3D morphology-based recomposition, including 2D morphology-based recomposition of 2D images in a 3D image dataset and in some examples, additional 1D morphology-based recomposition.

The method 1000 starts at 1002, wherein a 3D image dataset comprising an image stack of a plurality of 2D images is obtained. The 2D images may be taken at different focal planes with a step size therebetween, wherein the step size may be regular (e.g., each step size approximately equal to the other step sizes) or irregular (e.g., varying step sizes within the image stack). The step size may be at least equal to a size corresponding to one pixel. For example, the 3D image datasets may be taken by an imaging system (e.g., fluoroscopy imaging system) such as the system 100 of FIG. 1. As described above, the imaging system may impose a PSF resulting in reduced image quality, including reduced resolution, low contrast, increased background intensity and the like.

The method 1000 proceeds to 1004, wherein 2D morphology-based recomposition is applied to each 2D image of the plurality of 2D images in the image stack. For example, the method 300 of FIG. 3 may be applied to each of the plurality of 2D images. Thus, 1004 may include repeating a process through the image stack and for each of the plurality of 2D images, wherein the process includes performing a first white top hat (WTH) transform, a second WTH transform, and a third WTH transform on the input image to generate a first WTH transformed image, a second WTH transformed image, and a third WTH transformed image. Then, a first orthogonalized layer, a second orthogonalized layer, and a third orthogonalized layer may be generated based on the first WTH transformed image, the second WTH transformed image, and the third WTH transformed image, respectively. A first scaling factor may be calculated between the first orthogonalized layer and the second orthogonalized layer and a second scaling factor between the second orthogonalized layer and the third orthogonalized layer. A final image may be generated by applying the first scaling factor to the first orthogonalized layer and the second scaling factor to the second orthogonalized layer, the final image being a 2D morphology-based recomposition. In some examples, the final images produced from each 2D image are displayed in a second image stack with a display device and/or stored in memory. The second image stack may be a first 3D morphology-based recomposition of the 3D input image. The second image stack may be displayed with a display device and/or stored in memory.

The method 1000 proceeds to 1006, wherein 1D morphology-based recomposition is optionally applied to the 2D images perpendicular to the focal planes of the 2D images. The method 1006 may only occur for 3D image datasets having a regular step size. In other words, step 1006 is not included when applying morphology-based recomposition to 3D image datasets with irregular step size. For example, the method 300 of FIG. 3 may be applied repetitively to each pixel row perpendicular to the focal planes. The pixel rows may be parallel with a stacking axis along which the 2D images are stacked. The pixel rows may further be parallel with an optical axis of the imaging system which obtained the 3D image dataset (e.g., the optical axis 144 of FIG. 1). As such, 1006 may include loops to process through each pixel row and performing two or more 1D WTH transforms to generate two or more 1D WTH transformed layers for each pixel row. Two or more 1D orthogonalized layers may be generated from the two or more 1D WTH transformed layers. One or more scaling factors may be calculated and applied to the 1D orthogonalized layers of each pixel row to generate a final image stack, wherein the final image stack is a second 3D morphology-based recomposition of the 3D image dataset. The second 3D morphology-based recomposition (e.g. result of completing step 1006) may have a higher resolution than the first 3D morphology-based recomposition (e.g. result after completing step 1004 and not including step 1006) due to reducing the PSF along the stacking axis. The final image stack may be displayed with a display device and/or stored in memory. After 1004 or 1006, the method 1000 ends.

The method 1000 is exemplary and does not limit morphology-based recomposition of 3D image datasets according to the present disclosure. For example, the steps may be completed in a different order. The 1D morphology-based recomposition along the stacking axis of 1006 may be completed before the 2D morphology-based recompositions on each 2D image of 1004, in some examples.

Further, as described above, applying 2D morphology-based recomposition may be decomposed into two 1D morphology-based recompositions. Thus, alternatively to method 1000, 3D morphology-based recomposition may comprise performing a series of three 1D morphology-based recompositions along two or all of the three dimensions (e.g., x-axis, y-axis, and z-axis). A method 1010 is shown in FIG. 10B for applying a 3D morphology-based recomposition in such a way.

The method 1010 begins at 1012, wherein an input 3D image dataset is obtained. For example, the input 3D image dataset may comprise an image stack of a plurality of 2D images taken at different focal planes and stacked along a stacking axis. The input 3D image dataset may be obtained by an imaging system such as the system 100 of FIG. 1. The stacking axis may be parallel with an optical axis of the system such as the optical axis 144 of FIG. 1 and perpendicular to the focal planes. Step size between the focal planes may be regular or irregular, as described above with reference to FIG. 10A.

The method 1010 proceeds to 1014, wherein 1D morphology-based recomposition is applied to a first direction. For example, the first direction may be parallel with the focal planes of the images. However, in other examples, the first direction may be perpendicular to the focal planes. The method 300 of FIG. 3 may be applied to each pixel row of the input 3D image parallel with the first direction. As such, 1014 may include looping through each pixel row and performing two or more 1D WTH transforms to generate two or more 1D WTH transformed layers for each pixel row parallel with the first direction. Two or more 1D orthogonalized layers may be generated from the two or more 1D WTH transformed layers for each pixel row. One or more scaling factors may be calculated and applied to the 1D orthogonalized layers of each pixel row to generate a second image stack, wherein the second image stack is a first 3D morphology-based recomposition of the 3D image dataset. The first 3D morphology-based recomposition may have a higher resolution along the first direction than the input 3D image stack, due to reducing the PSF along the first direction.

The method 1010 proceeds to 1016, wherein 1D morphology-based recomposition is applied to a second direction perpendicular to the first direction. For example, if the first direction is parallel with the focal planes, the second direction may be either parallel with the focal planes or perpendicular to the focal planes. In examples wherein the first direction is perpendicular to the focal planes, the second direction is parallel with the focal planes. The method 300 of FIG. 3 may be applied to each pixel row of the first 3D morphology-based recomposition parallel with the second direction. As such, 1016 may include performing two or more 1D WTH transforms to generate two or more 1D WTH transformed layers for each pixel row parallel with the second direction. Two or more 1D orthogonalized layers may be generated from the two or more 1D WTH transformed layers. One or more scaling factors may be calculated and applied to the 1D orthogonalized layers of each pixel row to generate a third image stack, wherein the third image stack is a second 3D morphology-based recomposition of the 3D image dataset. The second 3D morphology-based recomposition may have a higher resolution than the first 3D morphology-based recomposition along the second direction due to additionally reducing the PSF in the second direction.

The method 1010 proceeds to 1018, wherein 1D morphology-based recomposition is optionally applied in a third direction perpendicular to the first direction and the second direction. Step 1018 is not included for 3D image datasets with irregular step size. As described above, 1D morphology-based recomposition may not be applied along a stacking axis with irregular step size. Thus, when applying the method 1010 to 3D image datasets with irregular step size, the method 1010 ends following 1016. However, for 3D image datasets with regular step size, the method 1010 may include 1018, in at least some examples. For example, if the first direction and the second direction are parallel with the focal planes, the third direction is perpendicular to the focal planes (e.g., parallel with the stacking axis). If the first direction is parallel with the focal planes and the second direction is perpendicular to the focal planes, the third direction is parallel with the focal planes. The method 300 of FIG. 3 may be applied to each pixel row of the second 3D morphology-based recomposition parallel with the third direction. As such, 1018 may include performing two or more 1D WTH transforms to generate two or more 1D WTH transformed layers for each pixel row parallel with the third direction. Two or more 1D orthogonalized layers may be generated from the two or more 1D WTH transformed layers for each pixel row. One or more scaling factors may be calculated and applied to the 1D orthogonalized layers of each pixel row to generate a final image stack, wherein the final image stack is a third 3D morphology-based recomposition of the 3D image dataset. The third 3D morphology-based recomposition may have a higher resolution than the first 3D morphology-based recomposition and the second 3D morphology-based recomposition along the third direction due to additionally reducing the PSF in the third direction. The method 1010 ends following 1016 or 1018.

The method 1010 is exemplary and the provided steps may take place in different orders than shown. For example, the series of 1D morphology-based recompositions on each pixel row of 1014, 1016, and 1018 may take place in succession (e.g., as three separate 1D operations) in any order of dimensions.

Either of the methods 1000 or 1010 of FIGS. 10A and 10B, respectively, may be applied to a 3D image dataset to produce a 3D morphology-based recomposition of the 3D image dataset. For example, a computing device (e.g., of an imaging system) may include a processor configured to execute instructions stored in non-transitory memory that, when executed, cause the processor to implement the methods 1000 and 1010. Executing the instructions may be initiated by receipt of an input image, wherein the input image may be obtained by fluorescence microscopy and/or the image may be a 3D image dataset. An example 3D morphology-based recomposition 760 resulting from applying 3D morphology-based recomposition to the 3D image dataset 700 (e.g., by method 1000 or method 1010) is shown in FIG. 7E.

Figure 7E:
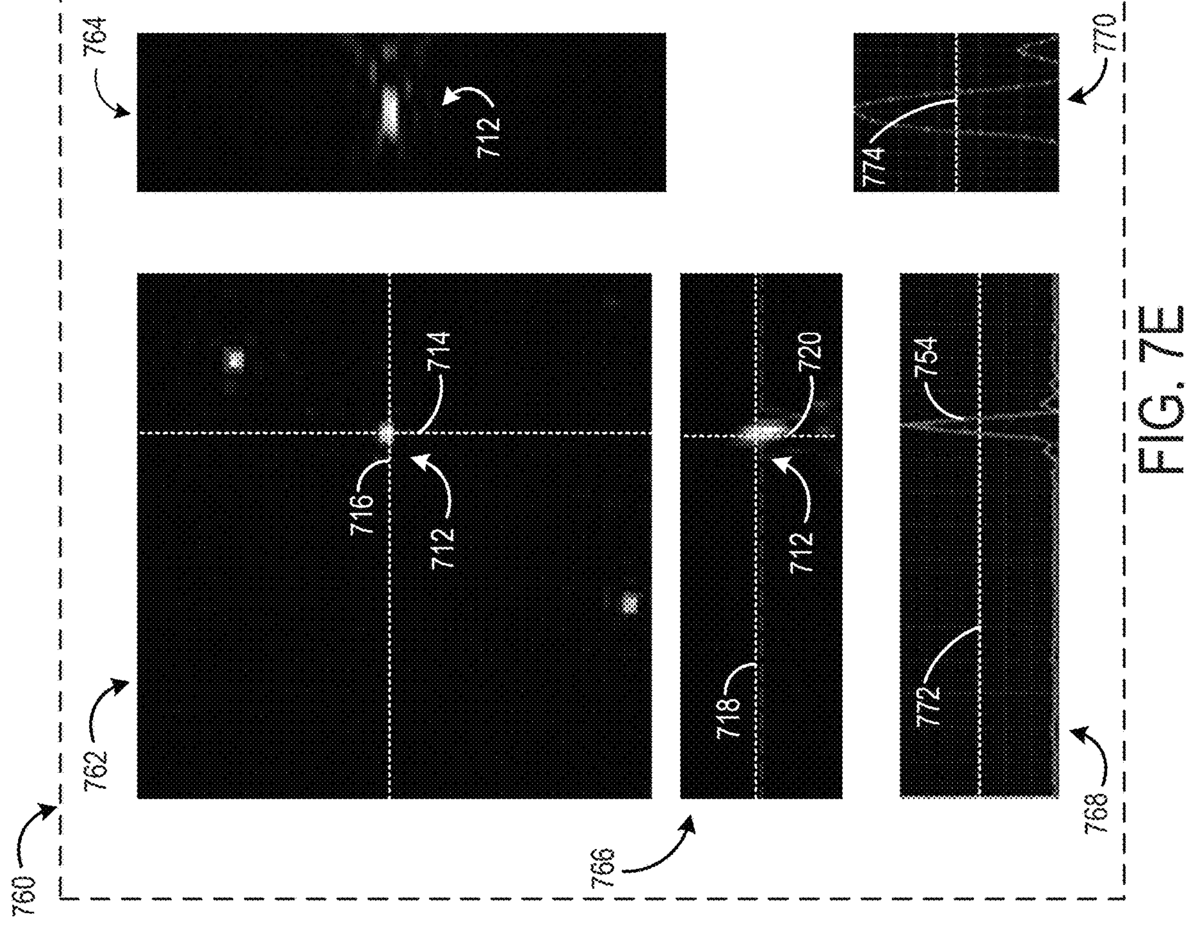

FIG. 7E shows an xy view 762, a yz view 764, and an xz view 766 of the image 760, wherein the yz view is taken along the axis 714, and the xz view is taken along the axis 716. The axis 714 and the axis 716 may intersect over the bead of interest 712. The 3D image dataset 760 may result from applying 3D morphology-based recomposition to the 3D image dataset 700 of FIG. 7A. For example, the 3D image dataset 760 may be produced from processing the 3D image dataset 700 by using the method 1000 of FIG. 10A including the optional step 1006, or by using the method 1010 of FIG. 10B including the optional step 1018.

An x-direction intensity plot 768 shows intensity along the axis 718 with an axis 772 marking the peak width at the half of maximum intensity in the plot 768, and a z-direction intensity plot 770 shows intensity along the axis 720 with an axis 774 marking the peak width at the half of the maximum intensity in the plot 770. The FWHM in the z-direction is reduced to 2.3 μm, showing increase in z-direction resolution from both the original 3D image dataset 700 of FIG. 7A (e.g., with z-direction FWHM of 4.9 μm) and the 2D morphology-based recomposition processed 3D image dataset 730 of FIG. 7B (e.g., with z-direction FWHM of 3.4 μm). A size of the bead of interest 712 in the xz view 766 and in the yz view 764 is also visibly reduced from the 3D image dataset 700 and the 3D image dataset 730. Thus, applying 3D morphology based recomposition to a 3D image dataset increases image quality compared to 2D deconvolution methods or 2D morphology based recomposition performed on each 2D image in the 3D image dataset.

Turning to FIG. 8A, another example is shown of a 3D image dataset 800 comprising an image stack of 9 2D images with a 5 μm step size along a stacking axis. Each of the 2D images is a 100×100 pixel image in an x-y plane. The z-axis may be the stacking axis along which the 2D images are stacked. The 3D image dataset 800 is of a plurality of hollow spheroids.

The 3D image dataset 800 is shown in an xy view 802, a yz view 804, and an xz view 806, wherein the yz view 804 is a section taken along a first axis 814, and the xz view 806 is a section taken along a second axis 816. The discretized appearance of the 3D image dataset 800 in the xz view 806 and the yz view 804 is due to the larger step size in the z direction. Reducing the step size may increase visual continuity in the xz view 806 and the yz view 804. However, the step size does not affect the effectiveness of the morphology-based recomposition methods disclosed herein in increasing image quality.

An x-direction intensity plot 808 shows an intensity along a third axis 818, and a z-direction intensity plot 810 shows an intensity along a fourth axis 820. The x-direction intensity plot 808 includes an x-direction intensity trace 854 and a fifth axis 822, and the z-direction intensity plot 810 includes a sixth axis 824, wherein the fifth axis 822 and the sixth axis 824 mark the span of intensity distribution at the half of the maximum intensity for purposes of visually showing the intensity values of the valleys in the respective intensity plots. As shown by local minima of the trace 854 having a greater intensity (e.g., 60% of maximum intensity) than the half intensity marked by the fifth axis 822 in in the x-direction intensity plot, background intensity is high in the 3D image dataset 800.

FIG. 8B shows 3D image dataset 830, wherein the 3D image dataset 830 results from applying 2D morphology-based recomposition to each 2D image in the 3D image dataset 800 (e.g., 9 2D images with z-step size 5 μm). The 3D image dataset 830 is shown in an xy view 832, a yz view 834, and an xz view 836, wherein the yz view 834 is a section taken along the first axis 814 and the xz view 836 is a section taken along the second axis 816.

An x-direction intensity plot 838 with the trace 854 and a seventh axis 842 marking half maximum shows that background intensity is reduced in the x-dimension compared to the plot 808 of FIG. 8A. For example, the local minima of the trace 854 are reduced in the 3D image dataset 830 (e.g., to 20% of the maximum intensity) compared to the 3D image dataset 800. A z-direction intensity plot 840 shows an eighth axis 844 marking half of the maximum intensity in the z-direction intensity plot 840. The FWHM of the peak shown in the z-direction intensity plot 840 is reduced compared to the z-direction intensity plot 810 of FIG. 8A. Thus, resolution along a stacking axis of an image stack may be increased by applying 2D morphology-based recomposition to each 2D image in the image stack.

As described above with reference to FIGS. 10A and 10B, applying 1D morphology-based recomposition along the stacking axis (e.g., z-direction) may be included in at least some examples to further increase the quality of the 3D image dataset 830 (e.g., reduce background intensity, increase resolution, etc.). Turning to FIG. 8C, a 3D image dataset 860 is shown, in an xy view 862, a yz view 864, and an xz view 866, wherein the 3D image dataset 860 is the result of applying additional 1D morphology-based recomposition to the 3D image dataset 830 of FIG. 8B along the z-axis. An x-direction intensity plot 868 shows the trace 854 of intensity along the section marked by the axis 818 with an axis 872 marking half of the maximum intensity of the plot 868. A z-direction intensity plot 870 shows intensity of the 3D image dataset 860 of a section along the axis 820, with an axis 874 marking half of the maximum intensity in the plot 870. As shown in the x-direction intensity plot 868, the valley intensity (e.g., local minima in the plot 868) are reduced further to nearly 0% intensity. Thus, background intensity is further reduced due to further narrowing of the PSF in the z-direction upon applying 1D morphology-based decomposition in the z-direction. As a result, the voids (e.g., hollow centers) and surface (e.g., membrane) textures of the spheroids in the xy view 862 have increased contrast compared to in the xy view 802 and the xy view 832 of FIGS. 8A and 8B, respectively. Further, the FWHM of the intensity peak shown in the z-direction intensity plot 870 is reduced, indicating an increased resolution along the z-axis (e.g., stacking axis, optical axis).

Thus, morphology-based recomposition methods are disclosed herein for processing (e.g., increasing resolution, reducing background noise, increasing contrast, etc.) of 2D and 3D images with 2D morphology-based recomposition and 3D morphology-based recomposition. Further, a morphology-based recomposition method may be used for applications wherein an image stack comprises a small number of 2D images, resulting in a "2.5 dimensional" (2.5D) image dataset, wherein a dimension along the optical axis is large enough to produce more than one 2D image with a given focus plane size, but not to produce a 3D image. 2.5D image datasets may be processed with some integration or projection, such as maximum intensity projection (MIP). An image resulting from integration or projection may include significant out-of-focus content, which causes poor image quality, including low resolution and contrast. Thus, morphology-based recomposition may be applied to each of the 2D image datasets prior to integration or projection to reduce out-of-focus content, thereby increasing image quality. The morphology-based recomposition method for processing 2.5D image datasets may be referred to herein as 2.5D morphology-based recomposition.

Turning to FIG. 11, a flowchart of an example of a method 1100 for 2.5D morphology-based recomposition is shown.

The method 1100 begins at 1102, wherein a 2.5D image dataset is obtained. For example, the 2.5D image dataset may be obtained by an imaging system such as the system 100 of FIG. 1. The 2.5D image dataset may comprise two or more 2D images in an image stack.

The method 1100 proceeds to 1104, wherein morphology based recomposition is applied to the 2.5D image dataset. For example, one of the method 1000 or the method 1010 of FIGS. 10A and 10B, respectively, may be implemented. Due to the small size of the dimension along the stacking axis (e.g., the z-axis), 1D morphology-based recomposition may not be applied along the stacking axis of the 2.5D image dataset. For example, the method 1000 of FIG. 10A may not include step 1006 when applied to a 2.5D image dataset. Likewise, the method 1010 of FIG. 10B may not include step 1018 when applied to a 2.5D image dataset.

The method proceeds to 1106, wherein an image integration or projection is applied to the 2.5D morphology-based recomposition. For example, MIP may aggregate the data from the 2D images in the image stack. Due to the reduced background intensity and increased resolution produced by completing 1104, the final image resulting from subsequently applying the integration or projection may be of higher quality than if the integration or projection alone was applied to the 3D image dataset obtained at 1102.

FIG. 9 shows an example image 900 wherein a first portion 902 has been processed with MIP alone (without morphology-based recomposition), and a second portion 904 has been processed with 2.5D morphology-based recomposition (e.g., as described above with regards to method 1100 in FIG. 11). The first portion 902 is the left side of the image 900 and the second portion 904 is the right side of the image 900. The second portion 904 shows more clearly defined features (e.g., higher resolution and contrast, less background intensity). Thus, 2.5D morphology-based recomposition may increase image quality (e.g., increase resolution and contrast, etc.) of a 2.5D image dataset.

The technical effect of generating a morphology-based recomposition based on an input image (e.g., 2D image or 3D image dataset) wherein the morphology-based recomposition is a final image generated from two or more orthogonalized layers strategically scaled with one or more scaling factors based on two or more structure element sizes and the instrument point spread function and image data is that image quality and image resolution is increased while reducing a time duration of computation and computational complexity when compared to 2D or 3D deconvolutions. As such, the process for generating the morphology-based recomposition may be automated and image processing may not rely on user intervention to generate final images with increased image quality. This may enable faster processing and throughput, as well as more efficient processing.

The disclosure also provides support for a system, comprising: a computing device including a processor configured to execute instructions stored in non-transitory memory that, when executed, cause the processor to: receive a 3D input image dataset comprising an image stack of a plurality of 2D images stacked along a stacking axis with a step size therebetween and for each of the plurality of 2D images: perform a first white top hat (WTH) transform, a second WTH transform, and a third WTH transform on the 2D image to generate a first WTH transformed image, a second WTH transformed image, and a third WTH transformed image, generate a first orthogonalized layer, a second orthogonalized layer, and a third orthogonalized layer based on the first WTH transformed image, the second WTH transformed image, and the third WTH transformed image, calculate a first scaling factor between the first orthogonalized layer and the second orthogonalized layer and a second scaling factor between the second orthogonalized layer and the third orthogonalized layer, generate a final image by applying the first scaling factor to the first orthogonalized layer and the second scaling factor to the second orthogonalized layer, the final image being a 2D morphology-based recomposition, and display the final images produced from each 2D image in a second image stack with a display device and/or store the second image stack in memory, the second image stack being a first 3D morphology-based recomposition of the 3D input image dataset. In a first example of the system, the 3D input image dataset is a fluorescent microscopy image. In a second example of the system, optionally including the first example, additional image processing is optionally performed on the first orthogonalized layer, the second orthogonalized layer, and the third orthogonalized layer. In a third example of the system, optionally including one or both of the first and second examples, the instructions are further executable to for each pixel row of the second image stack parallel with the stacking axis: perform two or more 1D WTH transforms to generate two or more 1D WTH transformed layers, generate two or more 1D orthogonalized layers from the two or more 1D WTH transformed layers, calculate one or more scaling factors, generate a final image stack by applying the one or more scaling factors to the two or more 1D orthogonalized layers of each pixel row to produce scaled 1D orthogonalized layers and summing the scaled 1D orthogonalized layers together, and display the final image stack with the display device and/or store the final image stack in memory, the final image stack being a second 3D morphology-based recomposition of the 3D input image dataset with a higher resolution than the first 3D morphology-based recomposition. In a fourth example of the system, optionally including one or more or each of the first through third examples, the instructions are further executable to apply an integration or projection to the second image stack to aggregate image data from each 2D image of the image stack.

The disclosure also provides support for a method, comprising: operating a computing device communicatively coupled to a microscopy system to generate a morphology-based recomposition based on a 3D input image dataset comprising an image stack of 2D images stacked along a stacking axis with a step size therebetween generated by the computing device based on signals received from a detector of the microscopy system, the morphology-based recomposition being a final image stack generated by applying a 1D morphology-based recomposition to each pixel row in a first direction, a second direction perpendicular to the first direction, and a third direction perpendicular to the first direction and the second direction, wherein applying the 1D morphology-based recomposition comprises: performing two or more 1D white top hat (WTH) transforms on the pixel row, generating two or more layers based on two or more WTH transformed pixel rows, and scaling pairs of adjacent layers based on one or more scaling factors, each scaling factor being based on an estimated point spread function to be reached, two structure element sizes, and image data. In a first example of the method, the two or more WTH transformed pixel rows are generated by performing two or more 1D WTH transforms based on structure elements of two or more sizes, each structure element being a different size and having a pre-determined value. In a second example of the method, optionally including the first example, the two or more layers comprises two or more orthogonalized layers, each orthogonalized layer being linearly independent. In a third example of the method, optionally including one or both of the first and second examples, each orthogonalized layer comprises one of a WTH transformed image generated with a smallest structure element or an image generated by subtracting one WTH transformed image with a smaller structure element from another WTH transformed image with a larger structure element. In a fourth example of the method, optionally including one or more or each of the first through third examples, the two or more orthogonalized layers comprises one of a top layer and a base layer or the top layer, one or more intermediate layers, and the base layer. In a fifth example of the method, optionally including one or more or each of the first through fourth examples, the top layer is computed with a smallest structure element and the base layer is computed with a largest structure element. In a sixth example of the method, optionally including one or more or each of the first through fifth examples, scaling pairs of adjacent image layers based on one or more scaling factors, each scaling factor being based on the estimated point spread function to be reached, two structure element sizes, and the image data comprises: calculating the one or more scaling factors between a pair of adjacent orthogonalized layers, and applying each scaling factor to a respective orthogonalized layer of the pair of adjacent orthogonalized layers and composing a final image based on one or more scaled orthogonalized layers.

The disclosure also provides support for a method, comprising: receiving a 3D input image dataset comprising an image stack of a plurality of 2D images stacked along a stacking axis with a step size therebetween and for each of the plurality of 2D images: performing a first white top hat (WTH) transform, a second WTH transform, and a third WTH transform on the 2D image to generate a first WTH transformed image, a second WTH transformed image, and a third WTH transformed image, generating a first orthogonalized layer, a second orthogonalized layer, and a third orthogonalized layer based on the first WTH transformed image, the second WTH transformed image, and the third WTH transformed image, calculating a first scaling factor between the first orthogonalized layer and the second orthogonalized layer and a second scaling factor between the second orthogonalized layer and the third orthogonalized layer, generating a final image by applying the first scaling factor to the first orthogonalized layer and the second scaling factor to the second orthogonalized layer, the final image being a 2D morphology-based recomposition, and displaying the final images produced from each 2D image in a second image stack with a display device and/or storing the final image in memory, the second image stack being a first 3D morphology-based recomposition of the 3D input image dataset. In a first example of the method, the method further comprises: for each pixel row of the second image stack parallel with the stacking axis: performing two or more 1D WTH transforms on the pixel row to generate two or more 1D WTH transformed layers, generating two or more 1D orthogonalized layers from the two or more 1D WTH transformed layers, calculating one or more scaling factors, generating a final image stack by applying the one or more scaling factors to the two or more 1D orthogonalized layers of each pixel row, and displaying the final image stack with the display device and/or storing the final image stack in memory, the final image stack being a second 3D morphology-based recomposition of the 3D input image dataset with a higher resolution than the first 3D morphology-based recomposition. In a second example of the method, optionally including the first example, the first WTH transform is performed with a first structure element of a first size, the second WTH transform is performed with a second structure element of a second size, and the third WTH transform is performed with a third structure element of a third size. In a third example of the method, optionally including one or both of the first and second examples, the first structure element is the smallest, the third structure element is the largest, and the second structure element is an intermediate size between the first structure element and the third structure element. In a fourth example of the method, optionally including one or more or each of the first through third examples, the first orthogonalized layer is the first WTH transformed image, the second orthogonalized layer is a difference between the second WTH transformed image and the first WTH transformed image, and the third orthogonalized layer is a difference between the third WTH transformed image and the second WTH transformed image. In a fifth example of the method, optionally including one or more or each of the first through fourth examples, the first orthogonalized layer is a top layer, the second orthogonalized layer is an intermediate layer, and the third orthogonalized layer is a base layer and additional image processing is optionally performed on the first orthogonalized layer, the second orthogonalized layer, and the third orthogonalized layer. In a sixth example of the method, optionally including one or more or each of the first through fifth examples, the first scaling factor is based on an estimated point spread function to be reached, the first size of the first structure element, the second size of the second structure element, an estimated point spread function of an imaging system, and image data, and wherein the second scaling factor is based on the estimated point spread function to be reached, the second size of the second structure element, the third size of the third structure element, and image data. In a seventh example of the method, optionally including one or more or each of the first through sixth examples, applying the first scaling factor and the second scaling factor comprises summing a product of the first orthogonalized layer and the first scaling factor, a product of the second orthogonalized layer and the second scaling factor, and the third orthogonalized layer to generate the final image.

As used herein, an element or step recited in the singular and preceded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A system, comprising:

a computing device including a processor configured to execute instructions stored in non-transitory memory that, when executed, cause the processor to:

receive a 3D input image dataset comprising an image stack of a plurality of 2D images stacked along a stacking axis with a step size therebetween and for each 2D image of the plurality of 2D images:

perform a first white top hat (WTH) transform, a second WTH transform, and a third WTH transform on the 2D image to generate a first WTH transformed image, a second WTH transformed image, and a third WTH transformed image;

generate a first orthogonalized layer, a second orthogonalized layer, and a third orthogonalized layer based on the first WTH transformed image, the second WTH transformed image, and the third WTH transformed image;

calculate a first scaling factor between the first orthogonalized layer and the second orthogonalized layer and a second scaling factor between the second orthogonalized layer and the third orthogonalized layer;

generate a final image by applying the first scaling factor to the first orthogonalized layer and the second scaling factor to the second orthogonalized layer, the final image being a 2D morphology-based recomposition; and display final images produced from each 2D image of the plurality of 2D images in a second image stack with a display device and/or store the second image stack in memory, the second image stack being a first 3D morphology-based recomposition of the 3D input image dataset.

2. The system of claim 1, wherein the 3D input image dataset is a fluorescent microscopy image.

3. The system of claim 1, wherein additional image processing is performed on the first orthogonalized layer, the second orthogonalized layer, and the third orthogonalized layer.

4. The system of claim 1, wherein the instructions are further executable to for each pixel row of the second image stack parallel with the stacking axis:

perform two or more 1D WTH transforms to generate two or more 1D WTH transformed layers; generate two or more 1D orthogonalized layers from the two or more 1D WTH transformed layers;

calculate one or more scaling factors;

generate a final image stack by applying the one or more scaling factors to the two or more 1D orthogonalized layers of the each pixel row to produce scaled 1D orthogonalized layers and summing the scaled 1D orthogonalized layers together; and display the final image stack with the display device and/or store the final image stack in memory, the final image stack being a second 3D morphology-based recomposition of the 3D input image dataset with a higher resolution than the first 3D morphology-based recomposition.

5. The system of claim 1, wherein the instructions are further executable to apply an integration or projection to the second image stack to aggregate image data from each 2D image of the second image stack.

6. A method, comprising: operating a computing device communicatively coupled to a microscopy system to generate a morphology-based recomposition based on a 3D input image dataset comprising an image stack of 2D images stacked along a stacking axis with a step size therebetween generated by the computing device based on signals received from a detector of the microscopy system, the morphology-based recomposition being a final image stack generated by applying a 1D morphology-based recomposition to each pixel row in a first direction and a second direction perpendicular to the first direction, wherein applying the 1D morphology-based recomposition comprises: performing two or more 1D white top hat (WTH) transforms on the each pixel row, generating two or more layers based on two or more WTH transformed pixel rows, and scaling pairs of adjacent layers based on one or more scaling factors, each scaling factor of the one or more scaling factors being based on an estimated point spread function to be reached, two structure element sizes, and image data.

7. The method of claim 6, wherein the two or more WTH transformed pixel rows are generated by performing two or more 1D WTH transforms based on structure elements of two or more sizes, each structure element being a different size and having a pre-determined value.

8. The method of claim 6, wherein the two or more layers comprises two or more orthogonalized layers, each orthogonalized layer being linearly independent.

9. The method of claim 8, wherein each orthogonalized layer comprises one of a WTH transformed image generated with a smallest structure element or an image generated by subtracting one WTH transformed image with a smaller structure element from another WTH transformed image with a larger structure element.

10. The method of claim 8, wherein the two or more orthogonalized layers comprises one of a top layer and a base layer or the top layer, one or more intermediate layers, and the base layer, and wherein the top layer is computed with a smallest structure element and the base layer is computed with a largest structure element.

11. The method of claim 6, wherein the method further comprises applying the 1D morphology-based recomposition in a third direction perpendicular to the first direction and the second direction.

12. The method of claim 6, wherein scaling pairs of adjacent image layers based on one or more scaling factors, each scaling factor being based on the estimated point spread function to be reached, two structure element sizes, and the image data comprises:
- calculating the one or more scaling factors between a pair of adjacent orthogonalized layers; and
- applying each scaling factor to a respective orthogonalized layer of the pair of adjacent orthogonalized layers and composing a final image based on one or more scaled orthogonalized layers.

13. A method, comprising:
- receiving a 3D input image dataset comprising an image stack of a plurality of 2D images stacked along a stacking axis with a step size therebetween and for each 2D image of the plurality of 2D images:
- performing a first white top hat (WTH) transform, a second WTH transform, and a third WTH transform on the 2D image to generate a first WTH transformed image, a second WTH transformed image, and a third WTH transformed image;
- generating a first orthogonalized layer, a second orthogonalized layer, and a third orthogonalized layer based on the first WTH transformed image, the second WTH transformed image, and the third WTH transformed image;
- calculating a first scaling factor between the first orthogonalized layer and the second orthogonalized layer and a second scaling factor between the second orthogonalized layer and the third orthogonalized layer;
- generating a final image by applying the first scaling factor to the first orthogonalized layer and the second scaling factor to the second orthogonalized layer, the final image being a 2D morphology-based recomposition; and
- displaying final images produced from each 2D image of the plurality of 2D images in a second image stack with a display device and/or storing the final image in memory, the second image stack being a first 3D morphology-based recomposition of the 3D input image dataset.

14. The method of claim 13, further comprising for each pixel row of the second image stack parallel with the stacking axis:
- performing two or more 1D WTH transforms on the pixel row to generate two or more 1D WTH transformed layers;
- generating two or more 1D orthogonalized layers from the two or more 1D WTH transformed layers;
- calculating one or more scaling factors;
- generating a final image stack by applying the one or more scaling factors to the two or more 1D orthogonalized layers of the each pixel row; and
- displaying the final image stack with the display device and/or storing the final image stack in memory, the final image stack being a second 3D morphology-based recomposition of the 3D input image dataset with a higher resolution than the first 3D morphology-based recomposition.

15. The method of claim 13, wherein the first WTH transform is performed with a first structure element of a first size, the second WTH transform is performed with a second structure element of a second size, and the third WTH transform is performed with a third structure element of a third size.

16. The method of claim 15, wherein the first structure element is the smallest, the third structure element is the largest, and the second structure element is an intermediate size between the first structure element and the third structure element.

17. The method of claim 13, wherein the first orthogonalized layer is the first WTH transformed image, the second orthogonalized layer is a difference between the second WTH transformed image and the first WTH transformed image, and the third orthogonalized layer is a difference between the third WTH transformed image and the second WTH transformed image.

18. The method of claim 13, wherein the first orthogonalized layer is a top layer, the second orthogonalized layer is an intermediate layer, and the third orthogonalized layer is a base layer and additional image processing is performed on the first orthogonalized layer, the second orthogonalized layer, and the third orthogonalized layer.

19. The method of claim 15, wherein the first scaling factor is based on an estimated point spread function to be reached, the first size of the first structure element, the second size of the second structure element, an estimated point spread function of an imaging system, and image data, and wherein the second scaling factor is based on the estimated point spread function to be reached, the second size of the second structure element, the third size of the third structure element, and the image data.

20. The method of claim 13, wherein applying the first scaling factor and the second scaling factor comprises summing a product of the first orthogonalized layer and the first scaling factor, a product of the second orthogonalized layer and the second scaling factor, and the third orthogonalized layer to generate the final image.

* * * * *